(12) United States Patent
Jiaang et al.

(10) Patent No.: US 12,246,021 B2
(45) Date of Patent: Mar. 11, 2025

(54) COMPOUNDS FOR USES IN PHARMACOLOGICAL INDUCTION OF HBF FOR TREATMENT OF SICKLE CELL DISEASE AND ß-THALASSEMIA

(71) Applicants: Academia Sinica, Taipei (TW); National Health Research Institutes, Miaoli County (TW)

(72) Inventors: Weir-Torn Jiaang, Miaoli County (TW); Che-Kun James Shen, Taipei (TW)

(73) Assignees: Academia Sinica, Taipei (TW); National Health Research Institutes, Miaoli County (TW)

( * ) Notice: Subject to any disclaimer, the term of this patent is extended or adjusted under 35 U.S.C. 154(b) by 792 days.

(21) Appl. No.: 17/439,630

(22) PCT Filed: Mar. 25, 2020

(86) PCT No.: PCT/US2020/024727
§ 371 (c)(1),
(2) Date: Sep. 15, 2021

(87) PCT Pub. No.: WO2020/198367
PCT Pub. Date: Oct. 1, 2020

(65) Prior Publication Data
US 2022/0152036 A1    May 19, 2022

Related U.S. Application Data

(60) Provisional application No. 62/823,990, filed on Mar. 26, 2019.

(51) Int. Cl.
*A61K 31/52*    (2006.01)
*A61K 31/5377*    (2006.01)
(Continued)

(52) U.S. Cl.
CPC .......... *A61K 31/52* (2013.01); *A61K 31/5377* (2013.01); *A61P 7/06* (2018.01); *C07D 473/16* (2013.01); *C07D 473/18* (2013.01)

(58) Field of Classification Search
CPC ....... A61K 31/52; A61K 31/5377; A61P 7/06; C07D 473/16
(Continued)

(56) References Cited

U.S. PATENT DOCUMENTS 6,767,906 B2    7/2004    Imbach et al.

FOREIGN PATENT DOCUMENTS

EP    1153024 B    4/2004
WO    2008128299 A    10/2008

OTHER PUBLICATIONS

Weatherall DJ. Phenotype[mdash]genotype relationships in monogenic disease: lessons from the thalassaemias. Nat Rev Genet. 2001;2(4):245-255.
(Continued)

*Primary Examiner* — Jeffrey S Lundgren
*Assistant Examiner* — Heather Dahlin
(74) *Attorney, Agent, or Firm* — BACON & THOMAS, PLLC

(57) ABSTRACT

Provided herein are compounds of Formula (I). The compounds described herein are useful in treating a disease associated with the expression of endogenous embryonic/fetal globin (e.g., γ globin) in erythrocytes (e.g., treating β-thalassemia and/or sickle cell disease through at least the induction of the globin gene expression in erythrocytes), and/or anemia (β-thalassemia and/or sickle cell anemia). The compounds described herein are useful in treating, delaying, and/or preventing the adverse effects of β-thalassemia and/or sickle cell disease, inducing γ globin produc-
(Continued)

tion, and/or inducing the expression of embryonic/fetal globin genes in a subject, cell, tissue, or biological sample. Also provided in the present disclosure are pharmaceutical compositions, kits, and methods of using the compounds for inducing γ globin production described herein and for treating any of the target diseases described herein.

(I)

32 Claims, 11 Drawing Sheets

(51) Int. Cl.
*A61P 7/06* (2006.01)
*C07D 473/16* (2006.01)
*C07D 473/18* (2006.01)

(58) Field of Classification Search
USPC .................................................. 514/252.16
See application file for complete search history.

(56) References Cited

OTHER PUBLICATIONS

Modell B. Global epidemiology of haemoglobin disorders and derived service indicators. Bulletin of the World Health Organization. 2008;2008(6):480-487.
Patrinos GP, Grosveld FG. Pharmacogenomics and therapeutics of hemoglobinopathies. Hemoglobin. 2008;32(1-2):229-236.
Schechter AN. Hemoglobin research and the origins of molecular medicine. Blood. 2008;112(10):3927-3938.
Platt OS, Brambilla DJ, Rosse WF, et al. Mortality in sickle cell disease. Life expectancy and risk factors for early death. N Engl J Med. 1994;330(23):1639-1644.
Scott MD, van den Berg JJ, Repka T, et al. Effect of excess alpha-hemoglobin chains on cellular and membrane oxidation in model beta-thalassemic erythrocytes. J Clin Invest. 1993;91(4):1706-1712.
Aljurf M, Ma L, Angelucci E, et al. Abnormal assembly of membrane proteins in erythroid progenitors of patients with beta-thalassemia major. Blood. 1996;87(5):2049-2056.
Natta CL, Niazi GA, Ford S, Bank A. Balanced globin chain synthesis in hereditary persistence of fetal hemoglobin. J Clin Invest. 1974;54(2):433-438.
Noguchi CT, Rodgers GP, Serjeant G, Schechter AN. Levels of fetal hemoglobin necessary for treatment of sickle cell disease. N Engl J Med. 1988;318(2):96-99.
Ley TJ, Nienhuis AW. Induction of hemoglobin F synthesis in patients with beta thalassemia. Annu Rev Med. 1985;36:485-498.
Humphries RK, Dover G, Young NS, et al. 5-Azacytidine acts directly on both erythroid precursors and progenitors to Increase production of fetal hemoglobin. J Clin Invest. 1985;75(2):547-557.
Olivieri NF, Weatherall DJ. The therapeutic reactivation of fetal haemoglobin. Hum Mol Genet. 1998;7(10):1655-1658.
McCaffrey PG, Newsome DA, Fibach E, Yoshida M, Su MS. Induction of gamma-globin by histone deacetylase Inhibitors. Blood. 1997;90(5):2075-2083.
Witt O, Monkemeyer S, Ronndahl G, et al. Induction of fetal hemoglobin expression by the histone deacetylase Inhibitor apicidin. Blood. 2003;101(5):2001-2007.
Constantoulakis P, Knitter G, Stamatoyannopoulos G. On the induction of fetal hemoglobin by butyrates: in vivo and in vitro studies with sodium butyrate and comparison of combination treatments with 5-AzaC and AraC. Blood. 1989;74(6):1963-1971.
Grigg A. Effect of hydroxyurea on sperm count, motility and morphology in adult men with sickle cell or myeloproliferative disease. Intern Med J. 2007;37(3):190-192.
Kinney TR, Helms RW, O'Branski EE, et al. Safety of hydroxyurea in children with sickle cell anemia: results of the HUG-KIDS study, a phase I/II trial. Pediatric Hydroxyurea Group. Blood. 1999;94(5):1550-1554.
Steinberg MH, Lu ZH, Barton FB, Terrin ML, Charache S, Dover GJ. Fetal hemoglobin in sickle cell anemia: determinants of response to hydroxyurea. Multicenter Study of Hydroxyurea. Blood. 1997;89(3):1078-1088.
Rule HG, Thompson SB. Acenaphthenone and acenaphthenequtnone. Journal of the Chemical Society. 1937:1761-1763.
Bistrzycki A, Risi J. On the effect of various diamines on naphthalic acid anhydride. Helvetica Chimica Acta. 1925;8:810-820.
Nam T-g, Lee J, Walker JR, Brinker A, Cho CY, Schultz PG. Identification and Characterization of Small-Molecule Inducers of Fetal Hemoglobin. ChemMedChem. 2011;6(5):777-780.
Fibach E, Prus E. Differentiation of Human Erythroid Cells in Culture. Current Protocols in Immunology. 2005;69(1):22F.27.21-22F.27.10.
Basak A, Sankaran VG. Regulation of the fetal hemoglobin silencing factor BCL11A. Annals of the New York Academy of Sciences. 2016;1368(1):25-30.
Akinsheye I, Alsultan A, Solovieff N, et al. Fetal hemoglobin in sickle cell anemia. Blood. 2011;118:19-27.
Imbach P, Capraro HG, Zimmermann J, Caravatti G, Furet P, Brill W, 2-amino-6-purines and their use as medicaments, Novartis-Erfindungen; Vienna, Austria), PCT document: WO/2000/049018A1.

Compound II

AS-28

| Compound | Rats IV (dose: 2.07 mg/kg) | | | | Rats PO (dose: 19.3 mg/kg) | | | | |
|---|---|---|---|---|---|---|---|---|---|
| | $T_{1/2}$ (hr) | CL (ml/min/kg) | $V_{ss}$ (l/kg) | $AUC_{(Total)}$ | $T_{1/2}$ (hr) | $C_{max}$ (ng/ml) | $T_{max}$ (hr) | $AUC_{(Total)}$ | F (%) |
| Compound II | 5.8 | 3.9 | 8.4 | 928.1 | 5.75 | 3.6 | 122 | 202.75 | 2.34 |

| Compound | Rats IV (dose: 5 mg/kg) | | | | Rats PO (dose: 20 mg/kg) | | | | |
|---|---|---|---|---|---|---|---|---|---|
| | $T_{1/2}$ (hr) | CL (ml/min/kg) | $V_{ss}$ (l/kg) | $AUC_{(0-inf)}$ (ng/mL * hr) | $T_{1/2}$ (hr) | $C_{max}$ (ng/ml) | $T_{max}$ (hr) | $AUC_{(0-inf)}$ (ng/mL * hr) | F (%) |
| AS-28 | 7.2 | 8.2 | 0.3 | 8862 | 3.8 | 2730 | 0.3 | 8996 | 25 |

| Compound | Rats IV (dose: 2 mg/kg) | | | | Rats PO (dose: 10 mg/kg) | | | | |
|---|---|---|---|---|---|---|---|---|---|
| | $T_{1/2}$ (hr) | CL (ml/min/kg) | $V_{ss}$ (l/kg) | $AUC_{(0-inf)}$ (ng/mL * hr) | $T_{1/2}$ (hr) | $C_{max}$ (ng/ml) | $T_{max}$ (hr) | $AUC_{(0-inf)}$ (ng/mL * hr) | F (%) |
| TN1 | 10.2 | 60.9 | 3.8 | 610 | ND | ND | ND | ND | ND |

HU-Resistant Cells

|  | Mock<br>N=7 | AS-28 (50mg)<br>N=6 | AS-28 (75mg)<br>N=7 | AS-28 (100mg)<br>N=5 |
|---|---|---|---|---|
| RBC (M/uL) | 7.23±0.75 | 7.78±0.58 | 7.89±0.43 | 8.05±0.62 |
| HGB (g/dL) | 7.46±0.7 | 8.15±0.68 | 8.23±0.41 | 8.05±0.7 |
| RET (%) | 57.34±3.67 | 58.98±3.18 | 57.51±3.55 | 54.66±2.3 |
| WBC (K/uL) | 34.15±5.85 | 35.85±3.37 | 35.75±3.43 | 44.12±6.63 |
| NEUT# (K/uL) | 13.39±4.65 | 15.05±2.89 | 12.15±2.73 | 15.64±3.47 |
| F-cell % | 1.63±0.11% | 2.15±0.14%** | 2.1±0.26% | 2.42±0.12%*** |
| HbF % | 0.20±0.02% | 0.28±0.02%* | 0.23±0.03% | 0.30±0.03%* |
| Sickle cells %<br>(hypoxia) | 16.78±1.9% | 10.0±1.4%* | 8.1±0.9%** | 8.8±0.8%** |

FIG. 5

| Top Canonical Pathways | | |
|---|---|---|
| Name | p-value | Overlap |
| Colanic Acid Building Blocks Biosynthesis | 6.07E-05 | 21.4 % 3/14 |
| GDP-mannose Biosynthesis | 4.66E-04 | 33.3 % 2/6 |
| UDP-N-acetyl-D-galactosamine Biosynthesis II | 1.68E-03 | 18.2 % 2/11 |
| Sertoli Cell-Sertoli Cell Junction Signaling | 3.47E-03 | 2.8 % 5/179 |
| Phagosome Maturation | 7.77E-03 | 2.9 % 4/138 |

FIG. 8

COMPOUNDS FOR USES IN PHARMACOLOGICAL INDUCTION OF HBF FOR TREATMENT OF SICKLE CELL DISEASE AND ß-THALASSEMIA

RELATED APPLICATIONS

This application claims the benefit of priority under 35 U.S.C. § 119(e) to U.S. Provisional Application, U.S. Ser. No. 62/823,990, filed Mar. 26, 2019, the contents of which are incorporated by reference herein in their entirety.

BACKGROUND OF THE INVENTION

The human α-like globin gene cluster [encoding ζ (embryonic) and α (fetal/adult) globin chains] and β-like globin gene cluster [encoding ε (embryonic), γ (fetal), and β (adult) globin chains] each extend over 50 kilobases on chromosomes 16 and 11, respectively. Human hemoglobin, a protein tetramer comprising two α-like globin chains and two β-like globin chains, functions as an oxygen transporter. Expression of the different globin chains is temporally controlled during development. For example, the first switch from embryonic to fetal hemoglobin occurs by silencing the embryonic globin genes and activating the fetal globin genes during pregnancy. The second switch from fetal to adult hemoglobin takes place in the newborn approximately six months after birth[1]. According to prevalence estimates by the World Health Organization (WHO), at least 5.2% of the world's population exhibit hemoglobin disorders, accounting for about 3.4% of deaths in children of less than 5 years of age[2]. These hemoglobin disorders are either structural disorders (in which the amino acid sequence is altered to produce abnormal hemoglobin) or expression defects of globin chain synthesis. In both cases, adult functional hemoglobin (HbA) deficiencies result in anemic syndromes such as sickle cell disease (SCD) and β-thalassemia (the two most common hemoglobinopathies), with approximately 4.5% of the global population suffering from either of these two diseases[3].

SCD is one of the most common monogenic disorders worldwide. Over 70% of SCD-affected newborns occur in Africa and it is estimated that more than 230,000 children with SCD are born in Africa every year. SCD is caused by a point mutation in the 17th nucleotide of the β globin gene (resulting in a glutamic acid to valine alteration). Mutant β globin chains polymerize under hypoxia, giving erythrocytes a sickle shape[4]. These sickle-shaped erythrocytes not only lose their ability to transport oxygen, but also obstruct capillaries to restrict blood flow to organs. As a consequence, vaso-occlusive crisis results in pain and organ damage (especially to the liver and heart). Moreover, these sickle-shaped erythrocytes lose their elasticity, leading to hemolytic crisis and anemia. With a high risk of early death, the life expectancy of SCD patients is reported to be shortened to an average of 42-48 years[5].

β-thalassemia is a hereditary anemia caused by mutations or deletions within the β-globin gene that reduce expression levels of β-globin chains. Due to lack of sufficient β-globin chains, the excess α-globin chains form toxic aggregates and bind to cell membranes, which induces rapid apoptosis of the erythrocytes during early erythroblast development[6,7].

Three exemplary therapeutic strategies have been used to modulate the anemia and related symptoms of severely hemoglobinopathic patients. The most common therapeutic strategy is regular transfusion throughout remaining lifespan to replenish the functional HbA required for survival. However, long-term transfusion is accompanied with a high risk of iron overload, which can cause tissue damage and organ dysfunction. To avoid the iron overload caused by transfusion, these chronically-transfused patients must receive regular and expensive iron chelation treatment. Alternatively, bone marrow transplantation represents another therapeutic strategy for severe SCD and β-thalassemia. Identification of a matched bone marrow donor is the primary limitation for this therapy, given the potential for a potent immune response after transplantation. Apart from these two traditional therapeutic strategies, pharmacologic induction of fetal hemoglobin (HbF) expression is a third strategy for modulating the hemoglobinopathic syndromes of patients suffering hemoglobin disorders. For β-thalassemia patients, elevation of fetal γ-globin chain synthesis can balance the excess of α globin chains by forming HbF, thereby modulating the severe anemia observed in these patients[8]. Moreover, increase γ-globin chain synthesis can prevent the formation of sickle-shaped hemoglobin (HbS), since HbF directly inhibits polymerization of HbS in SCD patients[9]. Thus, pharmaceutical induction of HbF in patients with hemoglobinopathies is a potentially useful therapeutic strategy. To date, several chemotherapeutic agents—such as trichostatin A (TSA) (histone deacetylase inhibitor), apicidin (histone deacetylase inhibitor), 5'-aza-cytidine (DNA methyltransferase inhibitor), hydroxyurea (HU) (ribonucleotide reductase inhibitor), sodium butyrate (NaB) and its derivatives (short-chain fatty acids, also known as histone deacetylase inhibitors)—have been demonstrated to stimulate fetal hemoglobin production[10-15]. Among them, HU is the only therapeutic medicine approved by the US Food & Drug Administration for the treatment of SCD, which induces expression of HbF for functional substitution of HbS in SCD patients. However, several side-effects of HU therapy have been reported, including leucopenia, thrombocytopenia, myelosuppression and potential reproductive toxicity[16,17]. In addition, at least 25% of SCD patients are poor or non-responders to HU treatment[18]. Thus, the identification of compounds that can induce the expression of endogenous embryonic/fetal globin chains as an alternative therapeutic strategy for these hemoglobinopathies is of clinical interest.

SUMMARY OF THE INVENTION

The present disclosure provides compounds, such as compounds of Formula (I), that inducing the expression of endogenous embryonic/fetal globin (e.g., γ globin) in erythrocytes. The compounds described herein may be useful in treating diseases associated with the expression of endogenous embryonic/fetal globin (e.g., γ globin) in erythrocytes, including the treatment of anemia such as β-thalassemia and/or sickle cell disease through at least the induction of the globin gene expression in erythrocytes. The compounds described herein may also be useful in treating, delaying, and/or preventing the adverse effects of β-thalassemia and/or sickle cell disease. The compounds described herein may also be useful in inducing γ globin production, and/or inducing the expression of embryonic/fetal globin genes in a subject, cell, tissue, or biological sample. Also provided are pharmaceutical compositions, kits, methods, and uses of any of the compounds described herein.

In one aspect, the present disclosure provides compounds of Formula (I):

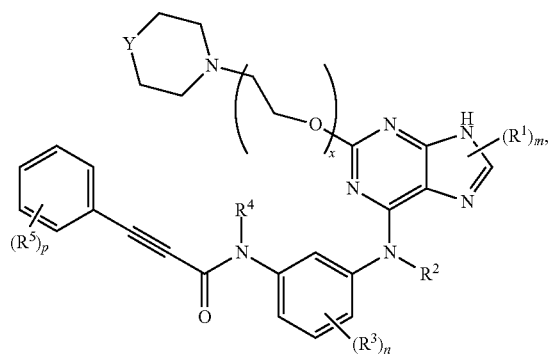

(I)

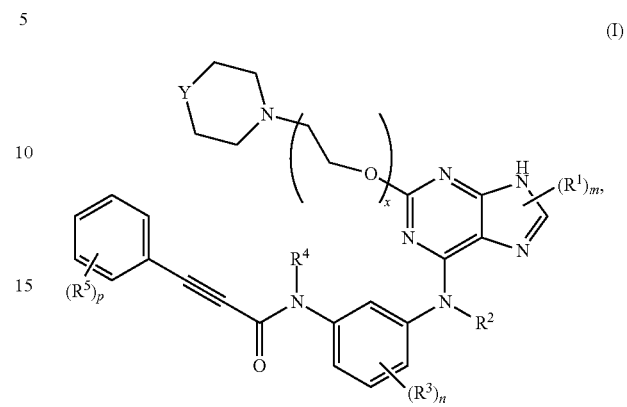

In one aspect, the present disclosure provides compounds of Formula (I):

(I)

or a pharmaceutically acceptable salt, co-crystal, tautomer, stereoisomer, solvate, hydrate, polymorph, isotopically enriched derivative, or prodrug thereof, wherein:
- each instance of $R^1$ is independently halogen, —C(=O)(alkyl); alkyl optionally substituted with halogen, unsubstituted alkenyl, unsubstituted alkynyl, or a nitrogen protecting group when attached to a nitrogen atom;
- $R^2$ is hydrogen, unsubstituted alkyl, or a nitrogen protecting group; each instance of $R^3$ is independently halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$OR^{D1}$, —$N(R^{D1a})_2$ or —$SR^{D1}$;
- $R^4$ is hydrogen, unsubstituted alkyl, or a nitrogen protecting group; each instance of $R^5$ is independently halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$OR^{D1}$, —$N(R^{D1a})_2$ or —$SR^{D1}$;
- $R^{D1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;
- each occurrence of $R^{D1a}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two instances of $R^{D1a}$ are taken together with their intervening atoms to form a substituted or unsubstituted heterocyclic or substituted or unsubstituted heteroaryl ring;
- Y is —O— or —N($R^6$)—;
- $R^6$ is hydrogen, optionally substituted alkyl, or a nitrogen protecting group;
- p is 0, 1, 2, 3, 4, or 5;
- m is 0, 1, or 2;
- n is 0, 1, 2, 3, or 4; and
- x is 0, 1, or 2.

or a pharmaceutically acceptable salt thereof, wherein: $R^1$, $R^2$, $R^3$, $R^4$, $R^5$, $R^6$, Y, m, n, p, and x are as described herein.

In certain embodiments, a compound of Formula (I) is of formula:

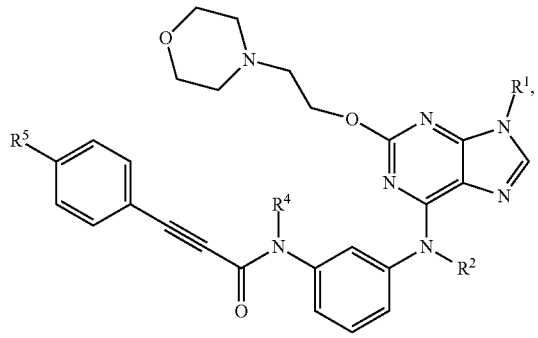

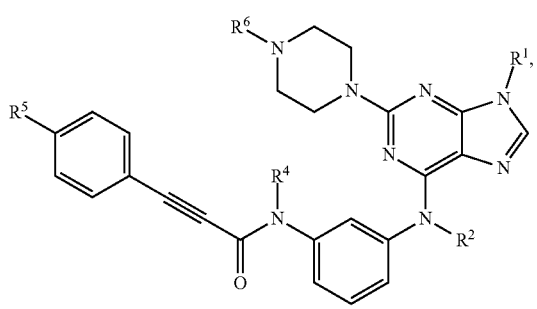

or a pharmaceutically acceptable salt, co-crystal, tautomer, stereoisomer, solvate, hydrate, polymorph, isotopically enriched derivative, or prodrug thereof, wherein $R^1$, $R^2$, $R^4$, $R^5$, and $R^6$ are as described herein.

Exemplary compounds of Formula (I) include, but are not limited to:

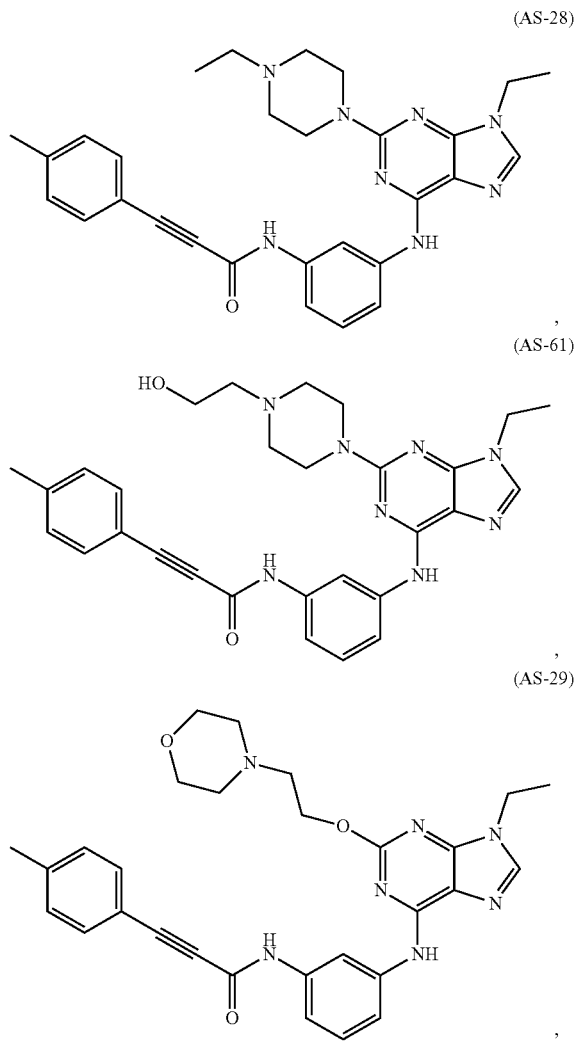

(AS-28)

(AS-61)

(AS-29)

or a pharmaceutically acceptable salt, co-crystal, tautomer, stereoisomer, solvate, hydrate, polymorph, isotopically enriched derivative, or prodrug thereof.

In another aspect, the present disclosure provides pharmaceutical compositions including one or more of the compounds described herein, and a pharmaceutically acceptable excipient. In certain embodiments, the pharmaceutical compositions described herein include an effective amount of a compound described herein for treating diseases associated with the expression of endogenous embryonic/fetal globin (e.g., γ globin) in erythrocytes, including the treatment of anemia such as β-thalassemia and/or sickle cell disease through at least the induction of the globin gene expression in erythrocytes. The pharmaceutical compositions described herein include an effective amount of a compound described herein for treating, delaying, and/or preventing the adverse effects of β-thalassemia and/or sickle cell disease. The pharmaceutical compositions described herein include an effective amount of a compound described herein for treating anemia in a subject in need thereof (e.g., wherein the subject suffers from or is suspected of having β-thalassemia and/or sickle cell anemia). The pharmaceutical compositions described herein include an effective amount of a compound described herein for inducing γ globin production, and/or inducing the expression of embryonic/fetal globin genes in a subject, cell, tissue, or biological sample. An effective amount described herein may be a therapeutically effective amount or prophylactically effective amount.

In yet another aspect, the present disclosure provides methods for treating diseases associated with the expression of endogenous embryonic/fetal globin (e.g., γ globin) in erythrocytes (e.g., treating β-thalassemia and/or sickle cell disease through at least the induction of the globin gene expression in erythrocytes), treating, delaying, and/or preventing the adverse effects of β-thalassemia and/or sickle cell disease, inducing γ globin production, and/or inducing the expression of embryonic/fetal globin genes in a subject, cell, tissue, or biological sample, the method comprising administering to a subject in need of the treatment, or contacting the cell, tissue, or biological sample with an effective amount of a compound or any of the pharmaceutical compositions described herein. The present disclosure provides methods for treating a subject with β-thalassemia or sickle cell anemia. The present disclosure provides methods for treating anemia in a subject in need thereof (e.g., wherein the subject suffers from or is suspected of having β-thalassemia and/or sickle cell anemia).

In certain embodiments, the subject being treated is a mammal (e.g., human or non-human mammal).

Another aspect of the present disclosure relates to kits comprising a container with a compound, or pharmaceutical composition thereof, as described herein. The kits described herein may include a single dose or multiple doses of the compound or pharmaceutical composition. The kits may be useful in a method of the disclosure. In certain embodiments, the kit further includes instructions for using the compound or pharmaceutical composition. The kit may also optionally include a device for administration of the compound or composition (e.g., a syringe such as a pre-filled syringe for parenteral administration).

In yet another aspect, the present disclosure provides compounds and pharmaceutical compositions described herein for use in treating a target disease such as a disease associated with the expression of endogenous embryonic/fetal globin (e.g., γ globin) in erythrocytes (e.g., treating β-thalassemia and/or sickle cell disease through at least the induction of the globin gene expression in erythrocytes), treating, delaying, and/or preventing the adverse effects of β-thalassemia and/or sickle cell disease, inducing γ globin production, and/or inducing the expression of embryonic/fetal globin genes in a subject, cell, tissue, or biological sample, as described herein and/or for manufacturing a medicament for use in treating the target disease. In another aspect, the present disclosure provides compounds and pharmaceutical compositions described herein for use in treating a subject with β-thalassemia or sickle cell anemia. In another aspect, the present disclosure provides compounds and pharmaceutical compositions described herein for use in treating anemia in a subject in need thereof (e.g., wherein the subject suffers from or is suspected of having β-thalassemia and/or sickle cell anemia).

The details of one or more embodiments of the disclosure are set forth herein. Other features, objects, and advantages of the disclosure will be apparent from the Detailed Description, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations, VCH Publishers, Inc., New York*, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —CH$_3$). In certain embodiments, the alkyl group is a substituted $C_{1-10}$ alkyl (such as substituted $C_{1-6}$ alkyl, e.g., —CF$_3$).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=CHCH$_3$ or

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of RC is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $BPh_4^-$, $Al(OC(CF_3)_3)_4^-$, and a carborane anion (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —CO$_2R^{aa}$, —C(=O)N($R^{bb}$)$_2$, —C(=NR$^{bb}$)$R^{aa}$, —C(=NR$^{bb}$)O$R^{aa}$, —C(=NR$^{bb}$)N($R^{bb}$)$_2$, —C(=O)NR$^{bb}$SO$_2R^{aa}$, —C(=S)N($R^{bb}$)$_2$, —C(=O)S$R^{aa}$, or —C(=S)S$R^{aa}$, wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=NR$^{bb}$)$R^{aa}$, —C(=NR$^{cc}$)O$R^{aa}$, —C(=NR$^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)(O$R^{cc}$)$_2$, —P(=O)($R^{aa}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rad groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2R^{aa}$, —SO$_2R^{aa}$, —C(=NR$^{cc}$)$R^{aa}$, —C(=NR$^{cc}$)O$R^{aa}$, —C(=NR$^{cc}$)N($R^{cc}$)$_2$, —SO$_2$N($R^{cc}$)$_2$, —SO$_2R^{cc}$, —SO$_2$O$R^{cc}$, —SOR$^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)O$R^{aa}$) include, but are not limited to, methyl carbamate, ethylcarbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Teroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4- pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), (3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, —R$^{aa}$, —C(=O)SR$^{aa}$, —C(=O)R$^{aa}$, —CO$_2$Ra, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a, 4,5,6,7,7a-octahydro-7,8,8-trimethyl-4,7-methanobenzofuran-2-yl, 1-ethoxyethyl, 1-(2-chloroethoxy) ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Exemplary sulfur atom substituents include, but are not limited to, —$R^{aa}$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3{}^+X^-$, —$P(OR^{cc})_2$, —$P(OR^{cc})_3{}^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein.

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms" or "carbon units") and does not include hydrogen atoms or heteroatoms. However, a non-chain substituent of a hydrocarbon chain may include any atoms, including hydrogen atoms, carbon atoms, and heteroatoms. For example, hydrocarbon chain —$C^AH(C^BH_2C^CH_3)$— includes one chain atom $C^A$, one hydrogen atom on $C^A$, and non-chain substituent —$(C^BH_2C^CH_3)$. The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —$CH(C_2H_5)$— is a $C_1$ hydrocarbon chain, and

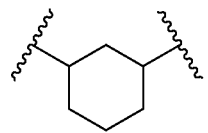 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —$(CH_2)_4$—). A hydrocarbon chain may also be unsaturated and include one or more C=C and/or C≡C bonds anywhere in the hydrocarbon chain. For instance, —CH=CH—$(CH_2)_2$—, —$CH_2$—C≡C—$CH_2$—, and —C≡C—CH=CH— are all examples of a unsubstituted and unsaturated hydrocarbon chain. In certain embodiments, the hydrocarbon chain is unsubstituted (e.g., —C≡C— or —$(CH_2)_4$—). In certain embodiments, the hydrocarbon chain is substituted (e.g., —$CH(C_2H_5)$— and —$CF_2$—). Any two substituents on the hydrocarbon chain may be joined to form an optionally substituted carbocyclyl, optionally substituted heterocyclyl, optionally substituted aryl, or optionally substituted heteroaryl ring. For instance,

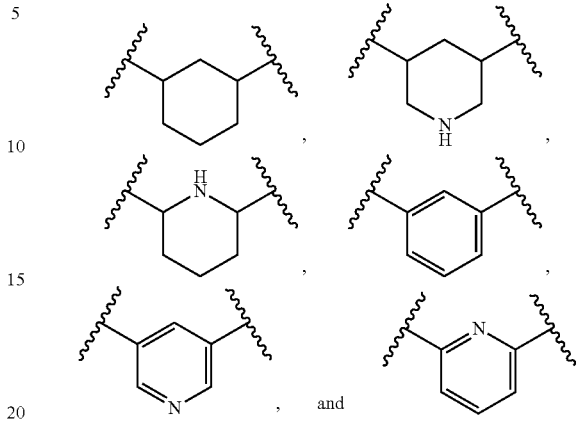

are all examples of a hydrocarbon chain. In contrast, in certain embodiments,

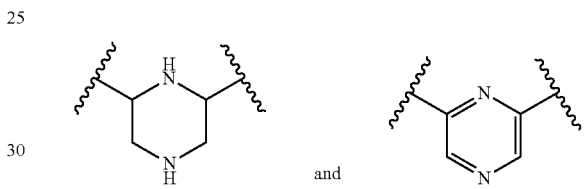

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

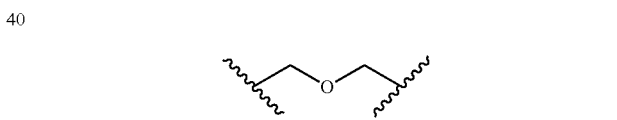

is a $C_3$ hydrocarbon chain wherein one chain atom is replaced with an oxygen atom. The term "leaving group" is given its ordinary meaning in the art of synthetic organic chemistry and refers to an atom or a group capable of being displaced by a nucleophile. See, for example, Smith, *March Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is an activated substituted hydroxyl group (e.g., —$OC(=O)SR^{aa}$, —$OC(=O)R^{aa}$, —$OCO_2R^{aa}$, —$OC(=O)N(R^{bb})_2$, —$OC(=NR^{bb})R^{aa}$, —$OC(=NR^{bb})OR^{aa}$, —$OC(=NR^{bb})N(R^{bb})_2$, —$OS(=O)R^{aa}$, —$OSO_2R^{aa}$, —$OP(R^{cc})_2$, —$OP(R^{cc})_3$, —$OP(=O)_2R^{aa}$, —$OP(=O)(R^{aa})_2$, —$OP(=O)(OR^{cc})_2$, —$OP(=O)_2N(R^{bb})_2$, and —$OP(=O)(NR^{bb})_2$, wherein $R^{aa}$, $R^{bb}$, and $R^{cc}$ are as defined herein). In some cases, the leaving group is a sulfonic acid ester, such as toluenesulfonate (tosylate, —OTs), methanesulfonate (mesylate, —OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, —OTf). In some cases, the leaving group is a brosylate, such asp-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference for the subject matter and purpose referenced herein. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R·xH$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R·0.5H$_2$O)), and polyhydrates (x is a number greater than 1, e.g., dihydrates (R·2H$_2$O) and hexahydrates (R·6H$_2$O)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy) alkyl esters or ((alkoxycarbonyl)oxy) alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The terms "composition" and "formulation" are used interchangeably.

A "subject" as used herein refers to a human (i.e., a male or a female of any age group, e.g., a pediatric subject (e.g., an infant, child, or an adolescent) or an adult subject (e.g., a young adult, a middle-aged adult, or a senior adult)). The subject may also include any non-human animals including, but not limited to a cynomolgus monkey or a rhesus monkey, a cattle, a pig, a horse, a sheep, a goat, a cat, a dog, a mouse, a rat, a rabbit, or a bird (e.g., a commercially relevant bird, such as a chicken, a duck, a goose, or a turkey). In certain embodiments, the non-human animal is a fish, a reptile, or an amphibian. In certain embodiments, the non-human animal is a mammal, a primate, a rodent, an avian, an equine, an ovine, a bovine, a caprine, a feline, or a canine. The non-human animal may be a male or a female at any stage of development. The non-human animal may be a transgenic animal or a genetically engineered animal. A "patient" refers to a human subject in need of treatment of a disease. The subject may also be a plant.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The terms "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen) to delay or prevent disease occurrence. Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response, i.e., treating the condition (therapeutically or prophylactically). As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay, minimize, or abolish one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The present invention provides exemplary endogenous embryonic/fetal globin chain inducers in a variety of formulations for therapeutic administration. In one aspect, the agents are formulated into pharmaceutical compositions by combination with appropriate, pharmaceutically acceptable carriers or diluents, and are formulated into preparations in solid, semi-solid, liquid or gaseous forms, such as tablets, capsules, powders, granules, ointments, solutions, suppositories, injections, inhalants, gels, microspheres, and aerosols. As such, administration is achieved in various ways. In some formulations, the inducers are systemic after administration; in others, the inhibitor is localized by virtue of the formulation, such as the use of an implant that acts to retain the active dose at the site of implantation.

As used herein, the terms "sickle cell disease" and "sickle cell anemia" are used interchangeably.

As used herein, the terms "determining", "assessing", "assaying", "measuring" and "detecting" refer to both quantitative and qualitative determinations and as such, the term "determining" is used interchangeably herein with "assaying," "measuring," and the like. Where a quantitative determination is intended, the phrase "determining an amount" and the like is used. Where either a qualitative or quantitative determination is intended, the phrase "determining a level" or "detecting a level" is used.

BRIEF DESCRIPTION OF THE DRAWINGS

FIG. 1A shows the structures of exemplary compounds II and AS-28 and their pharmacokinetic data. FIG. 1B shows the structure of exemplary compound TN1 and its pharmacokinetic data.

FIG. 4 shows that exemplary compound AS-28 reduces expression levels of the γ-globin gene repressor BCL11A.

FIG. 5 illustrates the dosage effect of treatment of SCD mice (an animal model of SCD disease in mice) versus control mice, with the indicated doses (50 mg, 75 mg, and 100 mg) of exemplary compound AS-28, showing this dosage effect on various parameters including red blood cell (RBC) numbers, hemoglobin levels, reticulocyte (RET), white blood cell (WBC), neutrophil (NEUT) values, and fetal hemoglobin (HbF). The abbreviations as defined as follows: RBC—red blood cells; HGB—hemoglobin; RET—reticulocytes; WBC—white blood cells; NEUT—neutrophils; HbF—fetal hemoglobin.

FIG. 8 shows the global effect of AS-28 on gene expression profile of human primary erythroid cells. The RNA-sequence data was analyzed by Ingenuity Pathways Analysis (IPA). The top cellular pathways in the primary erythroid cells affected by AS-28 are listed here. DEGs: Fold change ≥1.4, p<0.05.

FIG. 11 shows that exemplary compound AS-28 reduces expression levels of the γ-globin gene repressor BCL11A.

DETAILED DESCRIPTION

Figure 1A:
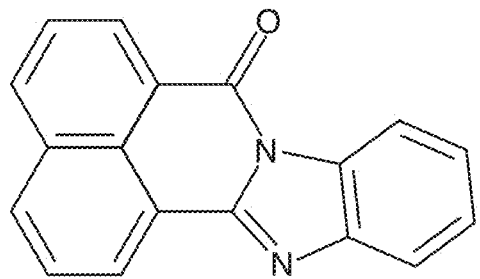
FIGS. 1A-1B show the structures of exemplary compounds II, AS-28 and TN1, together with their pharmacokinetic data, where rats were dosed with the indicated compounds via IV or PO as indicated. Exemplary compound II was dosed in rats via IV (2.07 mg/kg) and PO (19.3 mg/kg). Exemplary compound AS-28 was dosed in rats via IV (5.0 mg/kg) and PO (20.0 mg/kg). Exemplary compound TN1 was dosed in rats via IV (2.0 mg/kg) and PO (10.0 mg/kg). The abbreviations as defined as follows: IV—intravenous; PO—per-os (oral); $T_{1/2}$—half-life; CL—clearance; $V_{ss}$—steady-state distribution volume; AUC(0-inf)—area under the curve; F—bioavailability; ND—not detected.
Figure 1A:
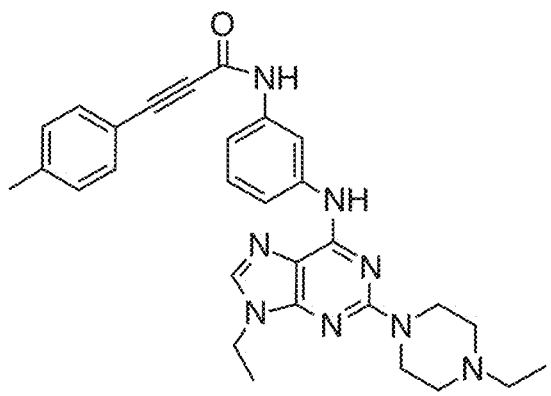

The present disclosure provides compounds of Formula (I) for treating a target disease such as a disease associated with the expression of endogenous embryonic/fetal globin (e.g., γ globin) in erythrocytes (e.g., treating β-thalassemia and/or sickle cell disease through at least the induction of the globin gene expression in erythrocytes). The compounds described herein are useful in treating, delaying, and/or preventing the adverse effects of β-thalassemia and/or sickle cell disease, inducing γ globin production, and/or inducing the expression of embryonic/fetal globin genes in a subject, cell, tissue, or biological sample. In another aspect, the present disclosure provides compounds for treating anemia in a subject in need thereof (e.g., wherein the subject suffers from or is suspected of having β-thalassemia and/or sickle cell anemia). Also provided in the present disclosure are pharmaceutical compositions, kits, and methods of using the compounds for inducing γ globin production described herein and for treating any of the target diseases described herein.

Minichromosome Maintenance Eukaryote Replicative Helicase (MCM) Inhibiting Compounds One aspect of the present disclosure relates to the inducers of γ globin production as described herein, as well as their pharmaceutically acceptable salts, solvates, hydrates, polymorphs, co-crystals, tautomers, stereoisomers, isotopically labeled derivatives, or prodrugs. These compounds are useful in treating diseases associated with the expression of endogenous embryonic/fetal globin (e.g., γ globin) in erythrocytes (e.g., treating β-thalassemia and/or sickle cell disease through at least the induction of the globin gene expression in erythrocytes), treating, delaying, and/or preventing the adverse effects of β-thalassemia and/or sickle cell disease, inducing γ globin production, and/or inducing the expression of embryonic/fetal globin genes in a subject, cell, tissue, or biological sample, and treating anemia in a subject in need thereof (e.g., wherein the subject suffers from or is suspected of having β-thalassemia and/or sickle cell anemia).

In certain embodiments, a compound described herein is of Formula (I):

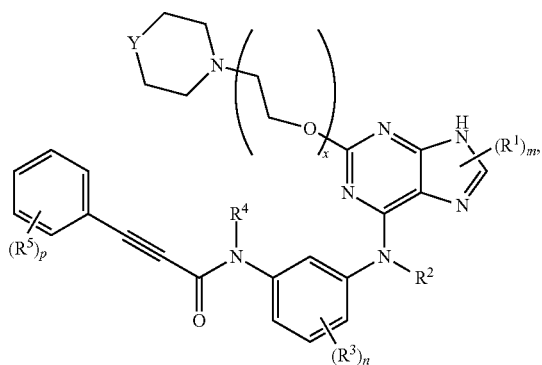

or a pharmaceutically acceptable salt, co-crystal, tautomer, stereoisomer, solvate, hydrate, polymorph, isotopically enriched derivative, or prodrug thereof, wherein: $R^1$, $R^2$, $R^3$, $R^4$, $R^5$, $R^6$, Y, m, n, p, and x are as described herein. In certain embodiments, a compound described herein is of Formula (I):

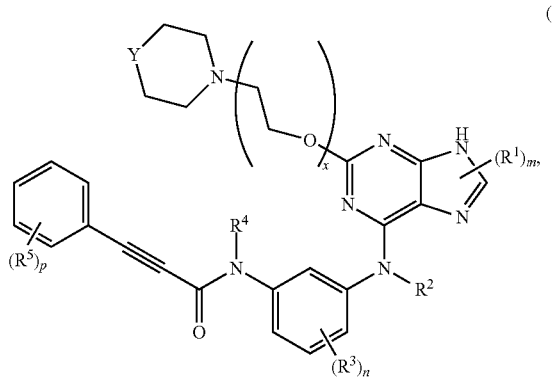

or a pharmaceutically acceptable salt thereof.

In some embodiments, Formula (I) includes zero or more instances of substituent $R^1$. In some embodiments, Formula (I) includes zero instances of substituent $R^1$. In some embodiments, Formula (I) includes one or more instances of substituent $R^1$. In certain embodiments, m is 0. In certain embodiments, m is 1. In certain embodiments, m is 2. In certain embodiments, at least one instance of $R^1$ is halogen (e.g., F, Cl, Br, or I). In certain embodiments, at least one instance of $R^1$ is —C(=O)(alkyl). In certain embodiments, at least one instance of $R^1$ is —C(=O)(optionally substituted alkyl). In certain embodiments, at least one instance of $R^1$ is —C(=O)(optionally substituted $C_1$-$C_6$ alkyl). In certain embodiments, at least one instance of $R^1$ is alkyl optionally substituted with halogen (e.g., F, Cl, Br, or I). In certain embodiments, at least one instance of $R^1$ is optionally substituted alkyl. In certain embodiments, at least one instance of $R^1$ is $C_1$-$C_6$ alkyl optionally substituted with halogen (e.g., F, Cl, Br, or I). In certain embodiments, at least one instance of $R^1$ is $C_1$-$C_6$ alkyl (e.g., unsubstituted methyl, unsubstituted ethyl, unsubstituted propyl, unsubstituted butyl). In certain embodiments, at least one instance of $R^1$ is unsubstituted methyl. In certain embodiments, at least one instance of $R^1$ is unsubstituted ethyl. In certain embodiments, m is 1; and at least one instance of $R^1$ is unsubstituted ethyl. In certain embodiments, at least one instance of $R^1$ is optionally substituted alkenyl (e.g., $C_2$-$C_6$ alkenyl). In certain embodiments, at least one instance of $R^1$ is optionally substituted $C_2$-$C_6$ alkenyl. In certain embodiments, at least one instance of $R^1$ is unsubstituted alkenyl. In certain embodiments, at least one instance of $R^1$ is unsubstituted $C_2$-$C_6$ alkenyl. In certain embodiments, at least one instance of $R^1$ is optionally substituted alkynyl (e.g., $C_2$-$C_{10}$ alkynyl). In certain embodiments, at least one instance of $R^1$ is optionally substituted $C_2$-$C_{10}$ alkynyl (e.g., optionally substituted, propynyl or butynyl). In certain embodiments, at least one instance of $R^1$ is unsubstituted alkynyl (e.g., unsubstituted $C_2$-$C_{10}$ alkynyl). In certain embodiments, at least one instance of $R^1$ is unsubstituted $C_2$-$C_{10}$ alkynyl (e.g., unsubstituted, propynyl or butynyl). In certain embodiments, at least one instance of $R^1$ is a nitrogen protecting group when attached to a nitrogen atom (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

Formula (I) includes substituent $R^2$. In some embodiments, $R^2$ is hydrogen. In some embodiments, $R^2$ is optionally substituted alkyl. In some embodiments, $R^2$ is optionally substituted $C_{1-6}$ alkyl. In certain embodiments, $R^2$ is $C_1$-$C_6$ alkyl optionally substituted with halogen (e.g., F, Cl, Br, or I). In some embodiments, $R^2$ is unsubstituted alkyl. In some embodiments, $R^2$ is unsubstituted $C_1$-$C_6$ alkyl (e.g., unsubstituted methyl, unsubstituted ethyl, unsubstituted propyl, unsubstituted butyl). In certain embodiments, at least one instance of $R^1$ is unsubstituted methyl. In certain embodiments, at least one instance of $R^1$ is unsubstituted ethyl. In some embodiments, $R^2$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In some embodiments, Formula (I) includes zero or more instances of substituent $R^3$. In some embodiments, Formula (I) includes zero instances of substituent $R^3$. In some embodiments, Formula (I) includes one or more instances of substituent $R^3$. In certain embodiments, n is 0. In certain embodiments, n is 1. In certain embodiments, n is 2. In certain embodiments, n is 3. In certain embodiments, n is 4. In certain embodiments, at least one instance of $R^3$ is halogen (e.g., F, Cl, Br, or I). In certain embodiments, at least one instance of $R^3$ is optionally substituted acyl (e.g., —C(=O)(alkyl)). In certain embodiments, at least one instance of $R^3$ is optionally substituted alkyl (e.g., optionally substituted $C_{1-6}$ alkyl). In certain embodiments, at least one instance of $R^3$ is optionally substituted $C_{1-6}$ alkyl (e.g., optionally substituted, methyl, ethyl, or propyl). In certain embodiments, at least one instance of $R^3$ is optionally substituted alkenyl (e.g., optionally substituted $C_2$-$C_6$ alkenyl). In certain embodiments, at least one instance of $R^3$ is optionally substituted alkynyl (e.g., optionally substituted $C_2$-$C_{10}$ alkynyl (e.g., optionally substituted, propynyl or butynyl)). In certain embodiments, at least one instance of $R^3$ can be optionally substituted carbocyclyl (e.g., substituted or unsubstituted, 3- to 7-membered, monocyclic carbocyclyl comprising zero, one, or two double bonds in the carbocyclic ring system). In some embodiments, at least one instance of $R^3$ can be optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In some embodiments, at least one instance of $R^3$ can be optionally substituted aryl (e.g., phenyl, or benzyl). In some embodiments, at least one instance of $R^3$ can be optionally substituted heteroaryl (e.g., 5- to 7-membered monocyclic heteroaryl, wherein one, two, three, or four atoms in the heteroaryl ring system are independently nitrogen, oxygen, or sulfur; or optionally substituted 8- to 10-membered bicyclic heteroaryl, wherein one, two, three, or four atoms in the heteroaryl ring system are independently nitrogen, oxygen, or sulfur). In some embodiments, at least one instance of $R^3$ can be —CN. In certain embodiments, at least one instance of $R^3$ is —$OR^{D1}$, —$N(R^{D1a})_2$ or —$SR^{D1}$, and $R^{D1}$ is as defined herein. In some embodiments, at least one instance of $R^3$ can be —$OR^D$, —$N(R^{D1a})_2$ or —$SR^{D1}$; wherein $R^{D1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom; each occurrence of $R^{D1a}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two instances of $R^{D1a}$ are taken together with their intervening atoms to form a substituted or unsubstituted heterocyclic or substituted or unsubstituted heteroaryl ring. In some embodiments, at least one instance of $R^3$ can be —$OR^{D1}$ (e.g., —OH or —OMe). In some embodiments, at least one instance of $R^3$ can be —$N(R^{D1a})_2$ (e.g., —$NH_2$ or —$NMe_2$). In some embodiments, at least one instance of $R^3$ can be —$SR^{D1}$ (e.g., —SH or —SMe).

In certain embodiments, $R^{D1}$ is hydrogen. In certain embodiments, $R^{D1}$ is optionally substituted acyl (e.g., —C(=O)Me). In certain embodiments, $R^{D1}$ is optionally substituted alkyl (e.g., substituted or unsubstituted $C_{1-6}$ alkyl). In certain embodiments, $R^{D1}$ is substituted or unsubstituted methyl. In certain embodiments, $R^{D1}$ is substituted or unsubstituted ethyl. In certain embodiments, $R^{D1}$ is substituted or unsubstituted propyl. In certain embodiments, $R^{D1}$ is optionally substituted alkenyl (e.g., substituted or unsubstituted $C_{2-6}$ alkenyl). In certain embodiments, $R^{D1}$ is optionally substituted alkynyl (e.g., substituted or unsubstituted $C_{2-6}$ alkynyl). In certain embodiments, $R^{D1}$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^{D1}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{D1}$ is optionally substituted aryl (e.g., substituted or unsubstituted, 6- to 10-membered aryl). In certain embodiments, $R^{D1}$ is benzyl. In certain embodiments, $R^{D1}$ is optionally substituted phenyl. In certain embodiments, $R^{D1}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{D1}$ is an oxygen protecting group when attached to an oxygen atom. In certain embodiments, $R^{D1}$ is a sulfur protecting group when attached to a sulfur atom.

In certain embodiments, at least one instance of $R^{D1a}$ is hydrogen. In certain embodiments, at least one instance of $R^{D1a}$ is optionally substituted acyl (e.g., —C(=O)Me). In certain embodiments, at least one $R^{D1a}$ is optionally substituted alkyl (e.g., substituted or unsubstituted $C_{1-6}$ alkyl). In certain embodiments, at least one instance of $R^{D1a}$ is substituted or unsubstituted methyl. In certain embodiments, at least one instance of $R^{D1a}$ is substituted or unsubstituted ethyl. In certain embodiments, at least one instance of $R^{D1a}$ is substituted or unsubstituted propyl. In certain embodiments, at least one instance of $R^{D1a}$ is optionally substituted alkenyl (e.g., substituted or unsubstituted $C_{2-6}$ alkenyl). In certain embodiments, at least one instance of $R^{D1a}$ is optionally substituted alkynyl (e.g., substituted or unsubstituted $C_{2-6}$ alkynyl). In certain embodiments, at least one instance of $R^{D1a}$ is optionally substituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{D1a}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{D1a}$ is optionally substituted aryl (e.g., substituted or unsubstituted, 6- to 10-membered aryl). In certain embodiments, at least one instance of $R^{D1a}$ is benzyl. In certain embodiments, at least one instance of $R^{D1a}$ is optionally substituted phenyl. In certain embodiments, at least one instance of $R^{D1a}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{D1a}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, two instances of $R^{D1a}$ are taken together with their intervening atoms to form a substituted or unsubstituted heterocyclic ring (e.g., substituted or unsubstituted, 5- to 10-membered monocyclic or bicyclic heterocyclic ring, wherein one or two atoms in the heterocyclic ring are independently nitrogen, oxygen, or sulfur) or substituted or unsubstituted heteroaryl ring (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

Formula (I) includes substituent $R^4$. In some embodiments, $R^4$ is hydrogen. In some embodiments, $R^4$ is optionally substituted alkyl. In some embodiments, $R^4$ is optionally substituted $C_{1-6}$ alkyl. In certain embodiments, $R^4$ is $C_1$-$C_6$ alkyl optionally substituted with halogen (e.g., F, Cl, Br, or I). In some embodiments, $R^4$ is unsubstituted alkyl. In some embodiments, $R^4$ is unsubstituted $C_1$-$C_6$ alkyl (e.g., unsubstituted methyl, unsubstituted ethyl, unsubstituted propyl, unsubstituted butyl). In certain embodiments, at least one instance of $R^4$ is unsubstituted methyl. In certain embodiments, at least one instance of $R^4$ is unsubstituted ethyl. In some embodiments, $R^4$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In some embodiments, $R^2$ is hydrogen and $R^4$ is hydrogen.

In some embodiments, Formula (I) includes zero or more instances of substituent $R^5$. In some embodiments, Formula (I) includes zero instances of substituent $R^5$. In some embodiments, Formula (I) includes one or more instances of substituent $R^5$. In certain embodiments, p is 0. In certain embodiments p is 1. In certain embodiments, p is 2. In certain embodiments, p is 3. In certain embodiments, p is 4. In certain embodiments, p is 5. In certain embodiments, at least one instance of $R^5$ is halogen (e.g., F, Cl, Br, or I). In certain embodiments, at least one instance of $R^5$ is optionally substituted acyl (e.g., —C(=O)(alkyl)). In certain embodiments, at least one instance of $R^5$ is optionally substituted alkyl (e.g., optionally substituted $C_{1-6}$ alkyl). In certain embodiments, at least one instance of $R^5$ is optionally substituted $C_{1-6}$ alkyl (e.g., optionally substituted, methyl, ethyl, or propyl). In certain embodiments, at least one instance of $R^5$ is unsubstituted alkyl. In certain embodiments, at least one instance of $R^5$ is unsubstituted $C_{1-6}$ alkyl (e.g., unsubstituted, methyl, ethyl, or propyl). In certain embodiments, at least one instance of $R^5$ is unsubstituted methyl. In certain embodiments, at least one instance of $R^5$ is unsubstituted ethyl. In certain embodiments, at least one instance of $R^5$ is unsubstituted propyl. In certain embodiments, at least one instance of $R^5$ is unsubstituted n-propyl. In certain embodiments, at least one instance of $R^5$ is unsubstituted isopropyl. In certain embodiments, at least one instance of $R^5$ is optionally substituted alkenyl (e.g., optionally substituted $C_2$-$C_6$ alkenyl). In certain embodiments, at least one instance of $R^5$ is optionally substituted alkynyl (e.g., optionally substituted $C_2$-$C_{10}$ alkynyl (e.g., optionally substituted, propynyl or butynyl)). In certain embodiments, at least one instance of $R^5$ can be optionally substituted carbocyclyl (e.g., substituted or unsubstituted, 3- to 7-membered, monocyclic carbocyclyl comprising zero, one, or two double bonds in the carbocyclic ring system). In some embodiments, at least one instance of $R^5$ can be optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In some embodiments, at least one instance of $R^5$ can be optionally substituted aryl (e.g., phenyl, or benzyl). In some embodiments, at least one instance of $R^5$ can be optionally substituted heteroaryl (e.g., 5- to 7-membered monocyclic heteroaryl, wherein one, two, three, or four atoms in the heteroaryl ring system are independently nitrogen, oxygen, or sulfur; or optionally substituted 8- to 10-membered bicyclic heteroaryl, wherein one, two, three, or four atoms in the heteroaryl ring system are independently nitrogen, oxygen, or sulfur). In some embodiments, at least one instance of $R^5$ can be —CN. In certain embodiments, at least one instance of $R^5$ is —$OR^{D1}$, —$N(R^{D1a})_2$ or —$SR^{D1}$; and $R^{D1}$ is as defined herein. In some embodiments, at least one instance of $R^5$ can be —$OR^{D1}$, —$N(R^{D1a})_2$ or —$SR^{D1}$; wherein $R^{D1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom; each occurrence of $R^{D1a}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two instances of $R^{D1a}$ are taken together with their intervening atoms to form a substituted or unsubstituted heterocyclic or substituted or unsubstituted heteroaryl ring. In some embodiments, at least one instance of $R^5$ can be —$OR^{D1}$ (e.g., —OH or —OMe). In some embodiments, at least one instance of $R^5$ can be —$N(R^{D1a})_2$ (e.g., —$NH_2$ or —$NMe_2$). In some embodiments, at least one instance of $R^5$ can be —$SR^{D1}$ (e.g., —SH or —SMe).

In Formula (I), Y is part of a six-membered heterocyclic ring. In some embodiments, Y is —O— or —N($R^6$)—; wherein $R^6$ is hydrogen, optionally substituted alkyl, or a nitrogen protecting group. In some embodiments, Y is —O— or —N($R^6$)—; wherein $R^6$ is optionally substituted alkyl. In some embodiments, Y is —O—. In some embodiments, Y is —N($R^6$)—, and $R^6$ is optionally substituted alkyl. In some embodiments, Y is —N($R^6$)—, and $R^6$ is optionally substituted $C_{1-6}$ alkyl. In certain embodiments, Y is —N($R^6$)—, and $R^6$ is unsubstituted $C_{1-6}$ alkyl (e.g., unsubstituted methyl, unsubstituted ethyl, unsubstituted propyl, unsubstituted butyl). In certain embodiments, Y is —N(unsubstituted ethyl)-. In certain embodiments, Y is —N($R^6$)—, wherein $R^6$ is of formula —$(CH_2)_{n1}(R^{6a})$, $R^{6a}$ is —OH or —O(optionally substituted alkyl), and n1 is 1, 2, 3, 4, 5, 6, or 7. In certain embodiments, n1 is 1. In certain embodiments, n1 is 2. In certain embodiments, n1 is 3. In certain embodiments, n1 is 4. In certain embodiments, n1 is 5. In certain embodiments, n1 is 6. In certain embodiments, n1 is 7. In certain embodiments, Y is —N($R^6$)—, wherein $R^6$ is of formula —$(CH_2)_{n1}(R^{6a})$, $R^{6a}$ is —OH or —O(unsubstituted alkyl), and n1 is 1, 2, 3, 4, or 5. In certain embodiments, Y is —N($R^6$)—, and $R^6$ is $C_{1-6}$ alkyl optionally substituted with —OH or —O(unsubstituted $C_{1-6}$ alkyl). In some embodiments, Y is —N($CH_2CH_2OH$)—.

In Formula (I), in some embodiments, x is 0, 1, or 2. In some embodiments, x is 0. In certain embodiments, x is 1. In certain embodiments, x is 2.

In some embodiments, a compound described herein is of Formula (I):

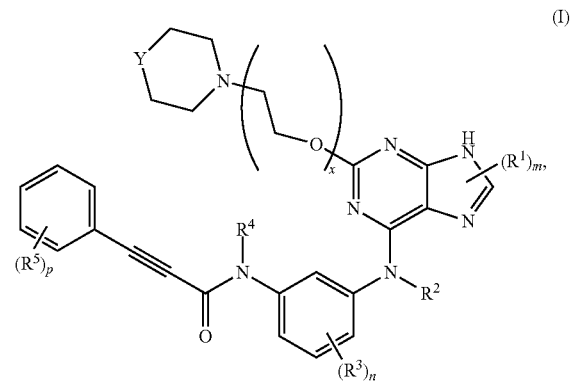

(I)

or a pharmaceutically acceptable salt, co-crystal, tautomer, stereoisomer, solvate, hydrate, polymorph, isotopically enriched derivative, or prodrug thereof, wherein:

each instance of $R^1$ is independently halogen, —C(=O)(alkyl); alkyl optionally substituted with halogen, unsubstituted alkenyl, or unsubstituted alkynyl;

$R^2$ is hydrogen or unsubstituted alkyl;

each instance of $R^3$ is independently halogen, optionally substituted acyl, optionally substituted alkyl, optionally substituted alkenyl, optionally substituted alkynyl, —CN, —$OR^{D1}$, —$N(R^{D1a})_2$ or —$SR^{D1}$;

$R^4$ is hydrogen or unsubstituted alkyl; each instance of $R^5$ is independently halogen, optionally substituted acyl, optionally substituted alkyl, optionally substituted alkenyl, optionally substituted alkynyl, —CN, —$OR^{D1}$, —$N(R^{D1a})_2$ or —$SR^{D1}$;

$R^{D1}$ is hydrogen, optionally substituted acyl, optionally substituted alkyl, optionally substituted alkenyl, optionally substituted alkynyl, or optionally substituted carbocyclyl; each occurrence of $R^{D1a}$ is hydrogen, optionally substituted acyl, optionally substituted alkyl, optionally substituted alkenyl, or optionally substituted alkynyl; or optionally two instances of $R^{D1a}$ are taken together with their intervening atoms to form a substituted or unsubstituted heterocyclic or substituted or unsubstituted heteroaryl ring;

Y is —O— or —$N(R^6)$—;

$R^6$ is hydrogen, optionally substituted alkyl, or a nitrogen protecting group;

p is 0, 1, 2, or 3;

m is 0, 1, or 2;

n is 0 or 1; and x is 0, 1, or 2.

In some embodiments, the compound of Formula (I) can be of one of the following formulae:

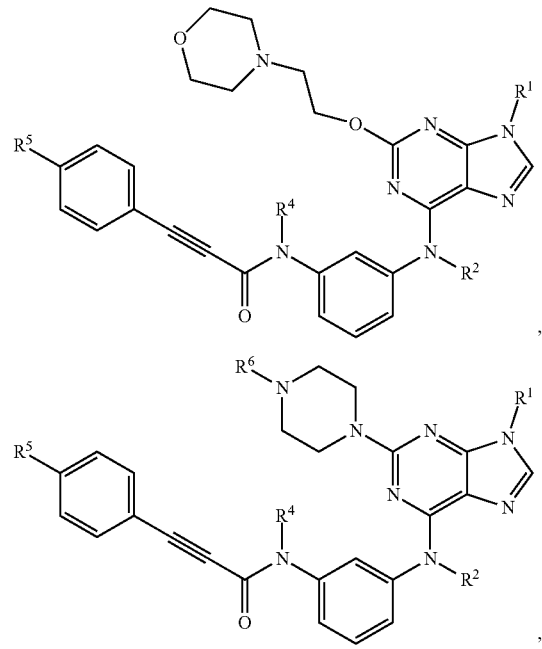

or a pharmaceutically acceptable salt, co-crystal, tautomer, stereoisomer, solvate, hydrate, polymorph, isotopically enriched derivative, or prodrug thereof.

In some embodiments, the compound of Formula (I) can be of one of the following formulae:

or a pharmaceutically acceptable salt thereof.

Exemplary compounds of Formula (I) are provided herein. In some embodiments, the compound of Formula (I) can be of one of the following formulae:

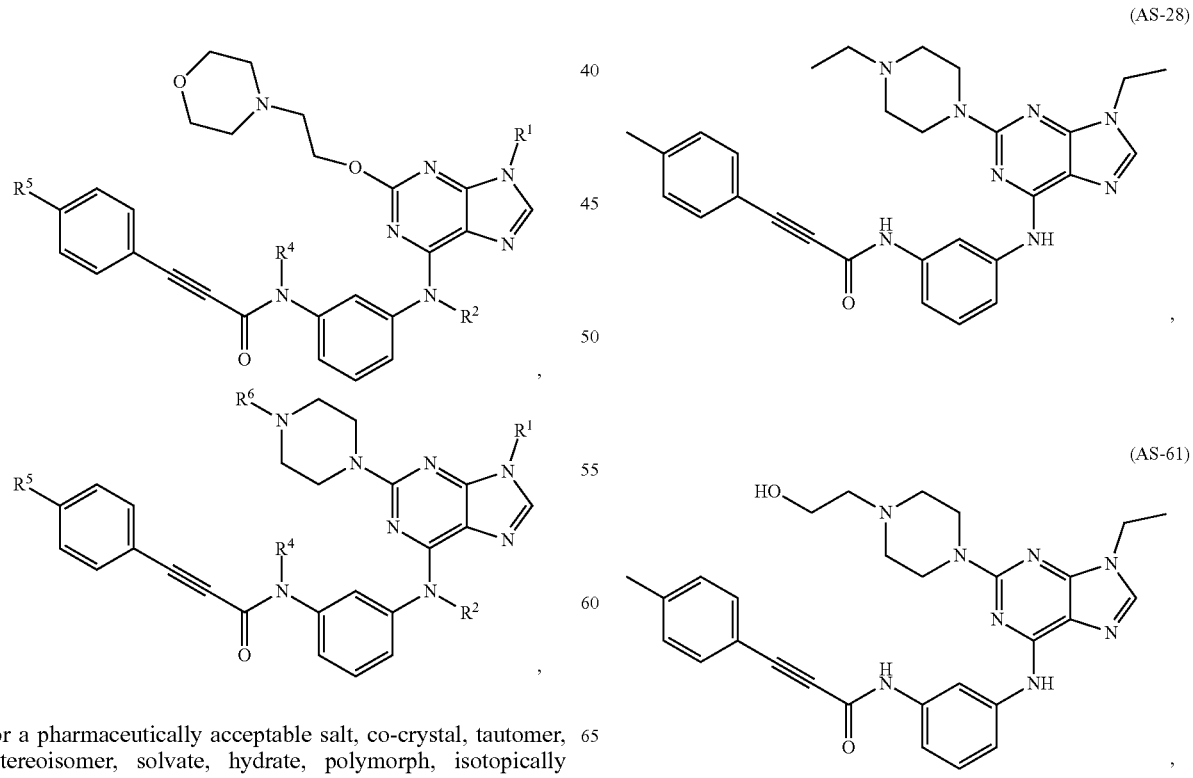

(AS-29)

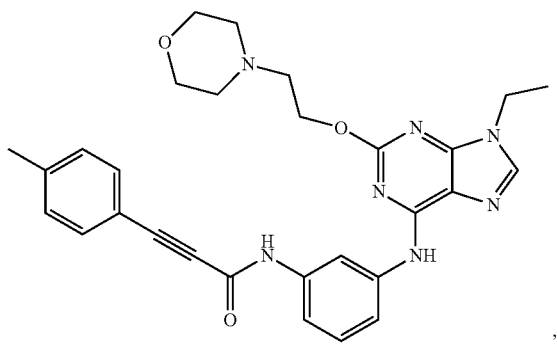

or a pharmaceutically acceptable salt, co-crystal, tautomer, stereoisomer, solvate, hydrate, polymorph, isotopically enriched derivative, or prodrug thereof. In some embodiments, the compound of Formula (I) can be of one of the following formulae:

(AS-28)

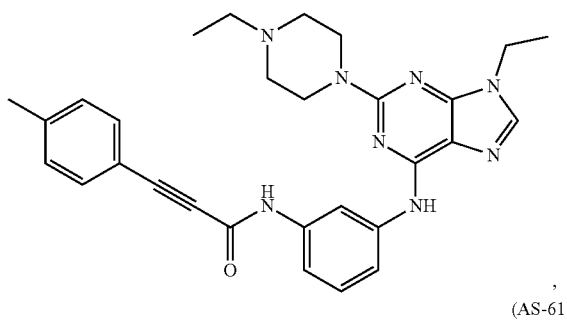

(AS-61)

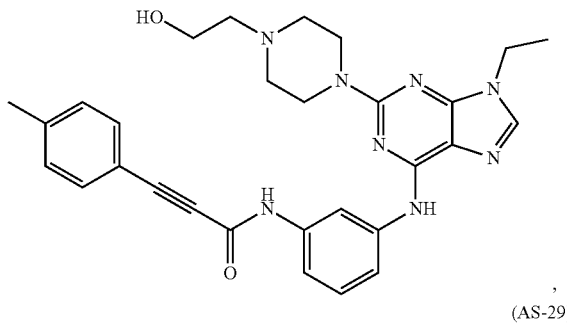

(AS-29)

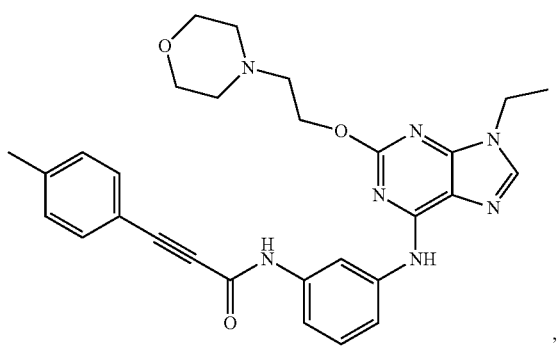

or a pharmaceutically acceptable salt thereof.

The compounds described herein can be prepared from readily available starting materials using methods known in the art. It will be appreciated that where typical or preferred process conditions (i.e., reaction temperatures, times, mole ratios of reactants, solvents, and pressures, etc.) are given, other process conditions can also be used unless otherwise stated. Optimum reaction conditions may vary with the particular reactants or solvents used, but such conditions can be determined by those skilled in the art by routine optimization procedures. The chemicals used in the above-described synthetic routes may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the compounds. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, Fieser and *Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The compounds of Formula (I) provided herein can be prepared from readily available starting materials using the following general methods and procedures. An exemplary schematic illustration for synthesizing the compounds described herein is provided in the Examples section below. Where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Pharmaceutical Compositions and Kits

The present disclosure provides pharmaceutical compositions comprising a compound described herein, or a pharmaceutically acceptable salt thereof, and optionally a pharmaceutically acceptable excipient. In certain embodiments, a pharmaceutical composition described herein comprises a compound described herein, or a pharmaceutically acceptable salt thereof, and a pharmaceutically acceptable excipient. The pharmaceutical compositions described herein are useful in treating a target disease such as a disease associated with the expression of endogenous embryonic/fetal globin (e.g., γ globin) in erythrocytes (e.g., treating β-thalassemia and/or sickle cell disease through at least the induction of the globin gene expression in erythrocytes). The pharmaceutical compositions described herein are useful in treating, delaying, and/or preventing the adverse effects of β-thalassemia and/or sickle cell disease, inducing γ globin production, and/or inducing the expression of embryonic/fetal globin genes in a subject, cell, tissue, or biological sample. The pharmaceutical compositions described herein are useful in treating anemia in a subject in need thereof (e.g., wherein the subject suffers from or is suspected of having β-thalassemia and/or sickle cell anemia).

In certain embodiments, a subject being treated herein is an animal. The animal may be of either sex and may be at any stage of development. In certain embodiments, the subject is a human. In certain embodiments, the subject is a mammal (e.g., non-human mammal). In certain embodiments, the subject is a domesticated animal, such as a dog, cat, cow, pig, horse, sheep, or goat. In certain embodiments, a subject being treated herein is a companion animal such as a dog or cat. In certain embodiments, a subject being treated herein is a livestock animal such as a cow, pig, horse, sheep, or goat. In certain embodiments, a subject being treated herein is a zoo animal. In another embodiment, a subject being treated herein is a research animal such as a rodent (e.g., mouse, rat), dog, pig, or non-human primate. In certain embodiments, the animal is a genetically engineered animal. In certain embodiments, the animal is a transgenic or genetically engineered animal (e.g., transgenic mice and transgenic pigs). In certain embodiments, the subject suffers from or is suspected of having β-thalassemia and/or sickle cell anemia.

In certain embodiments, the cell contacted with an effective amount of a compound or pharmaceutical composition described herein is in vitro. In certain embodiments, the contacted cell is ex vivo. In certain embodiments, the cell described herein is in vivo.

In certain embodiments, the compound described herein is provided in an effective amount in the pharmaceutical composition. In certain embodiments, the effective amount is a therapeutically effective amount (e.g., amount effective for treating a target disease such as a disease associated with the expression of endogenous embryonic/fetal globin (e.g., γ globin) in erythrocytes (e.g., treating β-thalassemia and/or sickle cell disease through at least the induction of the globin gene expression in erythrocytes), or treating anemia (e.g., wherein the subject suffers from or is suspected of having β-thalassemia and/or sickle cell anemia) in a subject in need thereof). In certain embodiments, the disease is associated with the expression of endogenous embryonic/fetal globin (e.g., γ globin) in erythrocytes. In certain embodiments, the disease is anemia. In certain embodiments, the disease is β-thalassemia and/or sickle cell disease. In certain embodiments, the disease is β-thalassemia and/or sickle cell anemia. In certain embodiments, the disease is treated through at least the induction of the globin gene expression in erythrocytes. In certain embodiments, the effective amount is a prophylactically effective amount (e.g., amount effective for preventing, delaying a disease associated with the expression of endogenous embryonic/fetal globin (e.g., γ globin) in erythrocytes (e.g., anemia (e.g., β-thalassemia and/or sickle cell anemia), or preventing the adverse effects of β-thalassemia and/or sickle cell disease). In certain embodiments, the effective amount is a therapeutically effective amount (e.g., amount effective for treating a disease associated with the expression of endogenous embryonic/fetal globin (e.g., γ globin) in erythrocytes (e.g., anemia (e.g., β-thalassemia and/or sickle cell anemia)).

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof. In certain embodiments, the composition of the instant disclosure is encapsulated in a carrier vehicle, which may be rigid vesicles, elastic vesicles, monolayer vesicles, multi-layer vesicles, liposomes, niosomes, proniosomes, Transfersomes®, ethosomes, L-595-PEG-8-L vesicles, nanoemulsions, nanosomes, nanoparticles, or a combination thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

In certain embodiments, a kit described herein includes a first container comprising a compound or pharmaceutical composition described herein. In certain embodiments, a kit described herein is useful in treating a disease associated with the expression of endogenous embryonic/fetal globin (e.g., γ globin) in erythrocytes (e.g., treating β-thalassemia and/or sickle cell disease through at least the induction of the globin gene expression in erythrocytes), and/or anemia (e.g., β-thalassemia and/or sickle cell anemia). In certain embodiments, the disease is anemia (e.g., β-thalassemia and/or sickle cell anemia) in a subject in need thereof. In some embodiments, the compounds described herein are useful in treating, delaying, and/or preventing the adverse effects of β-thalassemia and/or sickle cell disease, inducing γ globin production, and/or inducing the expression of embryonic/fetal globin genes in a subject, cell, tissue, or biological sample.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a treating a disease associated with the expression of endogenous embryonic/fetal globin (e.g., γ globin) in erythrocytes (e.g., treating β-thalassemia and/or sickle cell disease through at least the induction of the globin gene expression in erythrocytes), and/or anemia (e.g., β-thalassemia and/or sickle cell anemia) in a subject in need thereof, and/or treating, delaying, and/or preventing the adverse effects of β-thalassemia and/or sickle cell disease, inducing γ globin production, and/or inducing the expression of embryonic/fetal globin genes in a subject, cell, tissue, or biological sample. A kit described herein may include one or more additional pharmaceutical agents described herein as a separate composition.

Methods of Treatment

As shown in the Examples below, exemplary compounds described herein successfully induce γ-globin gene expression (e.g., induce γ-globin gene expression in hydroxyurea (HU)-resistant primary erythroid cells), reduce expression levels of the exemplary γ-globin gene repressor BCL11A, may target γ globin production, and contribute to inducing γ globin production in cells such as erythrocytes (e.g., primary erythroid cells).

Accordingly, the present disclosure provides methods of treating a disease associated with the expression of endogenous embryonic/fetal globin (e.g., γ globin) in erythrocytes (e.g., treating β-thalassemia and/or sickle cell disease through at least the induction of the globin gene expression in erythrocytes) in a subject in need thereof, the methods comprising administering to the subject an effective amount (e.g., therapeutically effective amount) of a compound, or pharmaceutical composition thereof, described herein. The present disclosure provides methods of treating anemia in a subject in need thereof (e.g., wherein the subject suffers from or is suspected of having β-thalassemia and/or sickle cell anemia).

Another aspect of the present disclosure relates to methods of preventing proliferative disease and/or infectious disease in a subject in need thereof, the methods comprising administering to the subject an effective amount (e.g., prophylactically effective amount) of a compound, or pharmaceutical composition thereof, described herein.

The compounds and pharmaceutical compositions described herein are useful in treating, delaying, and/or preventing the adverse effects of β-thalassemia and/or sickle cell disease, inducing γ globin production, and/or inducing the expression of embryonic/fetal globin genes in a subject, cell, tissue, or biological sample. In certain embodiments, the disease is anemia. In certain embodiments, the disease is β-thalassemia and/or sickle cell disease. In certain embodiments, the disease is β-thalassemia and/or sickle cell anemia. In certain embodiments, the disease is treated through at least the induction of the globin gene expression in erythrocytes.

In certain embodiments, the method described herein further includes administering to the subject an additional pharmaceutical agent. In certain embodiments, the method described herein further includes contacting the biological sample with an additional pharmaceutical agent. In certain embodiments, the method described herein further includes contacting the tissue with an additional pharmaceutical agent. In certain embodiments, the method described herein further includes contacting the cell with an additional pharmaceutical agent. In certain embodiments, the method described herein further includes a therapeutic for treating anemia (e.g., β-thalassemia and/or sickle cell disease).

The compounds and compositions provided herein can be administered by any route, including enteral (e.g., oral), parenteral, intravenous, intramuscular, intra-arterial, intracranial, intramedullary, intrathecal, subcutaneous, intraventricular, transdermal, intradermal, interdermal, rectal, intravaginal, intraperitoneal, topical (as by powders, ointments, creams, and/or drops), by any means that facilitate in vivo or ex vivo transport of the compound or composition as described herein in, into, or through tissue/skin of a subject (such as iontophoresis), mucosal, nasal, bucal, sublingual; by intratracheal instillation, bronchial instillation, and/or inhalation; and/or as an oral spray, nasal spray, and/or aerosol. In some embodiments, the pharmaceutical composition is administered orally or parentally. In some embodiments, the pharmaceutical composition is administered orally. In some embodiments, the pharmaceutical composition is administered parentally. Specifically contemplated routes are oral administration, intravenous administration (e.g., systemic intravenous injection), transfusion, perfusion, regional administration via blood and/or lymph supply, and/or direct administration to an affected site, such as intra-tumoral. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, biological sample, tissue, or cell. In certain embodiments, the duration between the first dose and last dose of the multiple doses is three months, six months, or one year. In certain embodiments, the duration between the first dose and last dose of the multiple doses is the lifetime of the subject, biological sample, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower, higher, or the same as that administered to an adult.

A compound or composition, as described herein, can be administered in combination with one or more additional pharmaceutical agents (e.g., therapeutically and/or prophylactically active agents) useful in treating disease associated with the expression of endogenous embryonic/fetal globin (e.g., γ globin) in erythrocytes (e.g., treating β-thalassemia and/or sickle cell disease through at least the induction of the globin gene expression in erythrocytes) in a subject in need thereof, and/or in treating, delaying, and/or preventing the adverse effects of a disease associated with the expression of endogenous embryonic/fetal globin (e.g., γ globin) in erythrocytes (e.g., treating β-thalassemia and/or sickle cell disease through at least the induction of the globin gene expression in erythrocytes) and/or anemia (e.g., β-thalassemia and/or sickle cell disease) in a subject in need thereof). The compounds or compositions can be administered in combination with additional pharmaceutical agents that improve their activity (e.g., activity (e.g., potency and/or efficacy) in treating a disease associated with the expression of endogenous embryonic/fetal globin (e.g., γ globin) in erythrocytes (e.g., treating β-thalassemia and/or sickle cell disease through at least the induction of the globin gene expression in erythrocytes) in a subject in need thereof, and/or in treating, delaying, and/or preventing the adverse effects of a disease associated with the expression of endogenous embryonic/fetal globin (e.g., γ globin) in erythrocytes (e.g., treating β-thalassemia and/or sickle cell disease through at least the induction of the globin gene expression in erythrocytes) and/or anemia (e.g., β-thalassemia and/or sickle cell disease) in a subject in need thereof), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, for different disorders, and/or it may achieve different effects. In certain embodiments, a pharmaceutical composition described herein including a compound described herein is administered to a patient in need thereof, to advantageously treat one or more diseases. In certain embodiments, said one or more diseases is a disease associated with the expression of endogenous embryonic/fetal globin (e.g., γ globin) in erythrocytes (e.g., β-thalassemia and/or sickle cell disease), anemia (e.g., β-thalassemia and/or sickle cell anemia), or a combination thereof. In a preferred embodiment, said one or more diseases is β-thalassemia, anemia, or a combination thereof.

The compound or composition may be administered concurrently with, prior to, or subsequent to one or more additional pharmaceutical agents, which may be useful as, e.g., combination therapies in treating, delaying, and/or preventing the adverse effects of a disease associated with the expression of endogenous embryonic/fetal globin (e.g., γ globin) in erythrocytes (e.g., β-thalassemia and/or sickle cell disease). In certain embodiments, the compound or composition described herein can be administered to a patient in need thereof, wherein the anemia (e.g., β-thalassemia and/or sickle cell anemia) of the patient is resistant to at least one pharmaceutical agent. In certain embodiments, the disease is anemia (e.g., β-thalassemia and/or sickle cell anemia) and said anemia (e.g., β-thalassemia and/or sickle cell anemia) is resistant to one or more anemia treatment agents including but not limited to hydroxyurea (HU). Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful in treating a disease associated with the expression of endogenous embryonic/fetal globin (e.g., γ globin) in erythrocytes, and/or anemia (e.g., β-thalassemia and/or sickle cell anemia). In certain embodiments, the additional pharmaceutical agent is a pharmaceutical agent useful in preventing a disease associated with the expression of endogenous embryonic/fetal globin (e.g., γ globin) in erythrocytes. In certain embodiments, the additional pharmaceutical agent is a pharmaceutical agent useful in treating anemia (e.g., β-thalassemia and/or sickle cell anemia). In certain embodiments, the additional pharmaceutical agent is a pharmaceutical agent approved by a regulatory agency (e.g., the US FDA) for treating and/or preventing a disease associated with the expression of endogenous embryonic/fetal globin (e.g., γ globin) in erythrocytes and/or anemia (e.g., β-thalassemia and/or sickle cell anemia). In certain embodiments, the additional pharmaceutical agent is a pharmaceutical agent approved by a regulatory agency (e.g., the US FDA) for treating and/or preventing anemia (e.g., β-thalassemia and/or sickle cell anemia). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the additional pharmaceutical agent is an anti-angiogenesis agent, anti-inflammatory agent, immunosuppressant, anti-bacterial agent, anti-viral agent, cardiovascular agent, cholesterol-lowering agent, anti-diabetic agent, anti-allergic agent, pain-relieving agent, or a combination thereof. In certain embodiments, the compounds described herein or pharmaceutical compositions can be administered in combination with anemia therapy.

Methods of Synthesis

An exemplary synthetic scheme for making the compounds described herein is as described previously. (See, Nam T-G et al., Identification and Characterization of Small-Molecule Inducers of Fetal Hemoglobin. *ChemMedChem.* 2011; 6(5):777-780; and Imbach P, et al., PCT document: WO/2000/049018A1, 2000; Published patents: EP1153024B1, 2004; U.S. Pat. No. 6,767,906B2, 2004). In one aspect, the present invention provides methods for preparing compounds of Formula (I).

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Example 1: Preparation of Exemplary Compounds

Figure 1B:
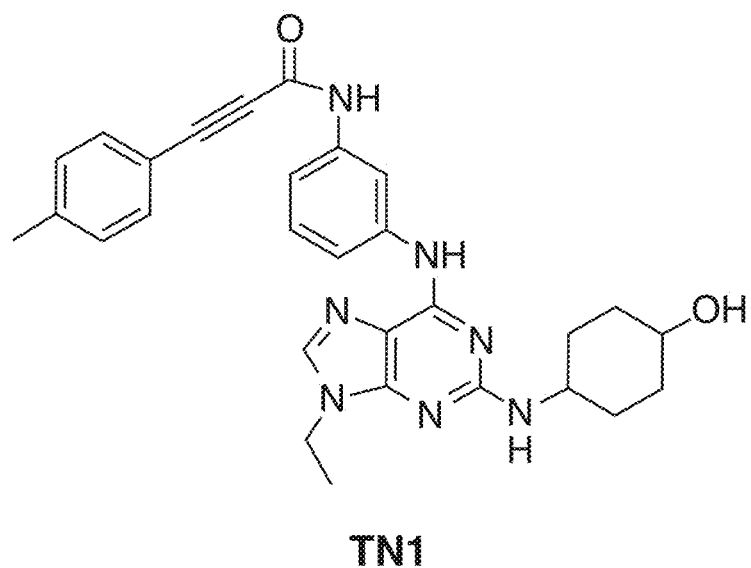

In a previous study, six asymmetric heterocyclic compounds that efficiently induce the expression of γ-globin in primary human erythroid cells were identified. These compounds shared an identical pharmacophore, which was previously described as a yellow dye[19,20]. Given its higher efficacy and specificity in the induction of γ-globin chains, compound II has the potential to be developed into a new generation of therapeutics for SCD and β-thalassemia. However, the solubility of asymmetric heterocyclic compound II is poor and it can only be dissolved in DMSO. Moreover, pharmacokinetic data revealed that the oral bioavailability of compound II is only 2.34% (FIGS. 1A-1B). Considering the disadvantages of compound II for further drug development, the pharmacophore of HbF-inducing compound TN1[21] was taken as a reference to design a new compound (AS-28). A pharmacokinetic study demonstrated that TN1 was not orally bioavailable in rats. Unexpectedly, it was found that exemplary compound AS-28 was an orally active compound, with an oral bioavailability in rats of approximately 25% (FIGS. 1A-1B). In this study, the HbF-inducing efficacy and therapeutic potential of AS-28 was established by using primary human erythroid cell cultures and an SCD mouse model. The possible biological mechanism underlying AS-28-mediated re-activation of γ-globin gene expression was also revealed.

Materials and Methods

Compound Synthesis

Figure 6:
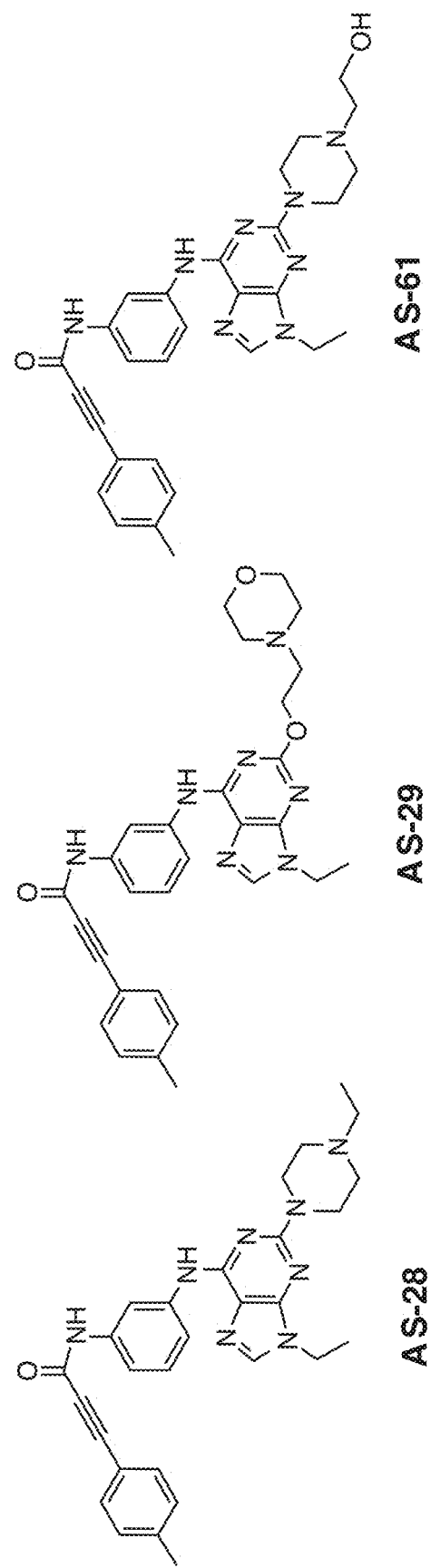
FIG. 6 shows the structures of exemplary representative compounds disclosed herein (AS-28, AS-29, and AS-61).

The 2-amino-6-anilino-purine compounds described in FIG. 6 can be prepared according to previously described methods[21,25]. Analytical data for the compounds are shown below.

3-p-Tolyl-propynoic acid {3-[9-ethyl-2-(4-ethylpiperazin-1-yl)-9H-purin-6-ylamino]phenyl}amide HCl salt (AS-28). $^1$H NMR (300 MHz, DMSO-d6): δ 10.92 (s, 1H), 10.77 (s, 1H), 10.39 (s, 1H), 8.83 (s, 1H), 8.56 (s, 1H), 7.56 (d, J=8.1 Hz, 2H), 7.44 (d, J=8.1 Hz, 1H), 7.35-7.30 (m, 3H), 7.16 (d, J=8.4 Hz, 1H), 4.82-4.77 (m, 2H), 4.21 (q, J=7.2 Hz, 2H), 3.56-3.38 (m, 4H), 3.19-2.98 (m, 4H), 2.37 (s, 3H), 1.46 (t, J=7.4 Hz, 3H), 1.27 (t, J=7.2 Hz, 3H); MS (ES$^+$) m/z calculated for $C_{29}H_{32}N_8$O: 508.27; found: 509.4 (M+H$^+$).

3-p-Tolyl-propynoic acid (3-{9-ethyl-2-[4-(2-hydroxyethyl)-piperazin-1-yl]-9H-purin-6-ylamino}phenyl)amide HCl salt (AS-061; AS-61). $^1$H NMR (400 MHz, DMSO-d$_6$): δ 11.02 (s, 1H), 10.77 (bs, 2H), 9.28 (s, 1H), 8.59 (s, 1H), 7.56 (d, J=8.0 Hz, 2H), 7.43 (d, J=8.8 Hz, 1H), 7.36-7.29 (m, 3H), 7.20 (d, J=8.0 Hz, 1H), 4.79-4.75 (m, 2H), 4.24 (q, J=7.2 Hz, 2H), 3.82 (t, J=5.0 Hz, 2H), 3.63-3.48 (m, 4H), 3.24-3.15 (m, 4H), 2.36 (s, 3H), 1.47 (t, J=7.2 Hz, 3H); MS (ES$^+$) m/z calculated for $C_{29}H_{32}N_8O_2$: 524.26; found: 525.2 (M+H$^+$).

3-p-Tolyl-propynoic acid {3-[9-ethyl-2-(2-morpholin-4-yl-ethoxy)-9H-purin-6-ylamino]phenyl}amide (AS-29). $^1$H NMR (300 MHz, DMSO-d$_6$): 10.87 (s, 1H), 9.97 (s, 1H), 8.35 (s, 1H), 8.19 (s, 1H), 7.59 (d, J=7.5 Hz, 2H), 7.63 (d, J=7.8 Hz, 2H), 7.32 (d, J=6.6 Hz, 1H), 4.47 (t, J=6.0, 5.9 Hz, 2H), 4.18 (q, J=14.4, 7.2 Hz, 2H), 3.60 (t, J=4.4, 4.2 Hz, 4H), 3.39 (s, 4H), 2.72 (t, J=5.9, 5.7 Hz, 2H), 2.54 (d, J=6.6 Hz, 2H), 2.42 (s, 3H), 1.46 (t, J=7.4, 7.2 Hz, 3H); MS (ES$^+$) m/z calcd. for $C_{29}H_{31}N_7O_3$: 525.25; found: 526.3 (M+H$^+$).

Example 2: Biological Assays of Exemplary Compounds

Primary Erythroid Cell Culture

Peripheral blood samples were purchased from the Taipei Blood Center. The concentrated blood was diluted 1:5 (V/V) in phosphate-buffered saline (PBS) and distributed in a thin layer on Ficoll-paque PLUS (d=1.007 g/ml) (GE Healthcare) in a SepMate column (STEMCELL). After centrifugation at 1200 g for 10 minutes, the cells in the inter-phase region were collected. The collected cells were washed with PBS and centrifuged at low speed three times. The remaining mononuclear cells were expanded in Phase I medium containing 1×SFEM (STEMCELL), 100 ng/ml SCF, 20 ng/ml IL-3, 20 ng/ml IL-6, and 100 ng/ml Flt3-L at 37° C. in an incubator with 5% $CO_2$ for 7 days. The expanded mononuclear cells were further differentiated in Phase II medium containing 1×SFEM (StemSpan), 20 ng/ml SCF, 5 ng/ml IL-3, 1 U/ml EPO for another 7 days. The differentiated erythroid cells were treated with indicated compounds of different dosages with a seeding density of 5×10$^5$ cells/ml for another 3 days.

Quantitative RT-PCR

After 3 days of compound treatment, total RNA was extracted by a Quick-RNA miniprep kit (Zymo) and reverse-transcription was performed using Maxima H Minus Reverse Transcriptase (ThermoFisher Scientific) according to the manufacturer's instructions. Quantitative PCR was performed on a LightCycler system with SYBR green master mix following the manufacturer's instructions (Roche). The relative quantitative RT-PCR data was normalized to the Cq number of β-actin and compared to a mock control.

Cell Viability Assay

Cell viability was assessed using AlamarBlue reagent (Invitrogen). After 3 days of treatment, 100 μl of treated cell culture was transferred into a 96-well plate and 1/10 volume of AlamarBlue reagent was added and the cell culture was incubated overnight at 37° C. Cell viability was evaluated using a multi-label counter (Ex 530-560 nm, Em 590 nm) (PerkinElmer).

Western Blot Analysis

After 3 days of treatment, total protein was extracted by modified RIPA (50 mM Tris-HCl pH7.8, 150 mM NaCl, 1% NP-40, 0.5% sodium deoxycholate, 0.1% SDS, 1 mM EGTA, 5 mM EDTA, 10 mM NaF, 1 mM NaV$_3$O$_4$ and 1× complete EDTA-free Protease Inhibitor Cocktail). 30 µg of protein extracts were separated by 10% SDS-PAGE and the resulting gel was blotted onto PVDF membrane. After blocking with 5% non-fat milk in TBST, the membrane was incubated overnight with primary antibody against BCL11A or β-actin at 4° C. After incubating with horseradish peroxidase-conjugated secondary antibodies and washing the blot, the signals of indicated proteins were visualized by ECL (PerkinElmer) following the manufacturer's protocol.

Mice

Sickle cell disease mice (B6; 129-Hba$^{tm1(HBA)Tow}$, Hbb$^{tm2(HBG1,HBB*)Tow}$/J) were purchased from Jackson Laboratory and were bred at the AS Core, Academia Sinica. Mice of 6-8 weeks old were used for experiments. Treatment groups received vehicle [20% (2-Hydroxypropyl)-β-cyclo-dextrin] plus AS-28 (50 mg/kg, 75 mg/kg or 100 mg/kg), which was administered by oral gavage twice per day, 5 days per week, for 4 weeks.

Complete Blood Count Analysis

Blood was collected by submandibular blood collection and analysis was performed using a ProCyte Dx automatic analyzer.

F-Cell Quantitation

10 µl of whole blood was washed twice with PBS and then fixed with 0.05% glutaraldehyde for 10 minutes. After fixation, the cells were washed twice with PBS and then permeabilized by adding cold 0.1% Triton X-100 for 5 minutes. Cells were washed twice with 0.1% BSA/PBS and stained with PE-HbF antibody (BD) for 40 minutes at room temperature (with protection from light). Finally, the cells were washed three times with 0.1% BSA/PBS and passed through a 0.3 µM cell strainer (Falcon). F-cell % was analyzed by flow cytometry (LSRII-18P, BD).

Hemoglobin High-Performance Liquid Chromatography (HPLC)

50 µl of whole blood was lysed in 200 µl ddH$_2$O and centrifuged for 5 minutes at 13,000 rpm to extract the hemolysate. HPLC was performed according to a previously described protocol[22].

Blood Smear

For hypoxia treatment, whole blood was incubated in a hypoxic incubator chamber (3% O2) for 30 minutes. 2 l of whole blood (with or without hypoxia) was used to make blood smears on slides. Slides were air-dried and then stained with Liu-stain before quantifying the percentage of sickle-shaped cells.

Exemplary Effects of Exemplary Compound AS-28 in Erythroid Cells

AS-28 can Induce γ-Globin Expression in Primary Human Erythroid Cell Culture

Figure 2:
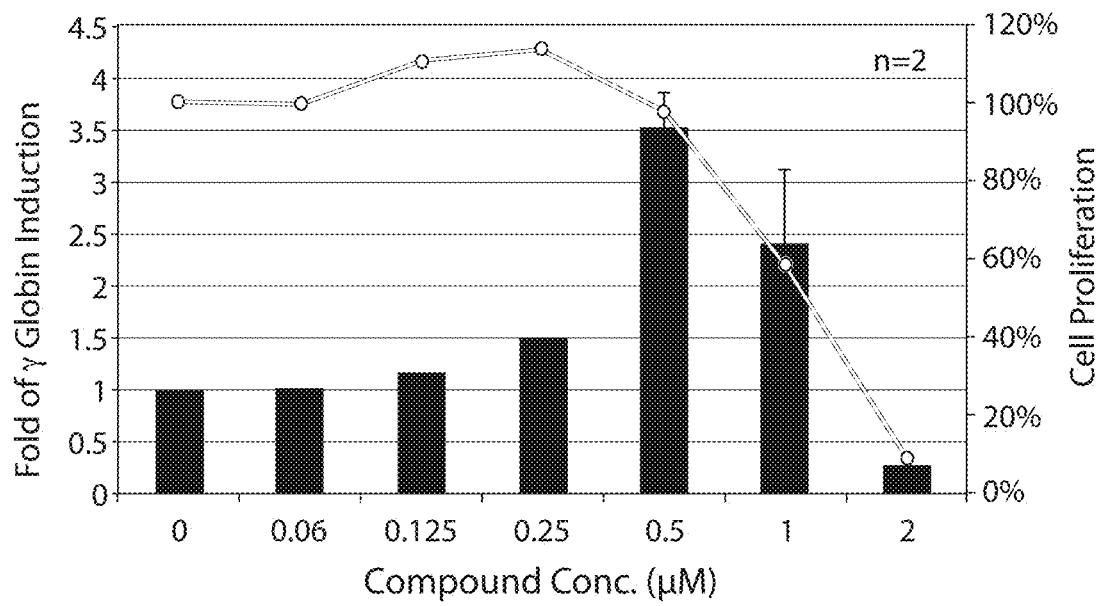
FIG. 2 is a graph showing dose-dependent γ-globin gene induction by exemplary compound AS-28, by the concentration of AS-28 compared with the fold level of γ-globin induction and percentage of cell proliferation in primary human erythroid cell cultures.
Figure 9:
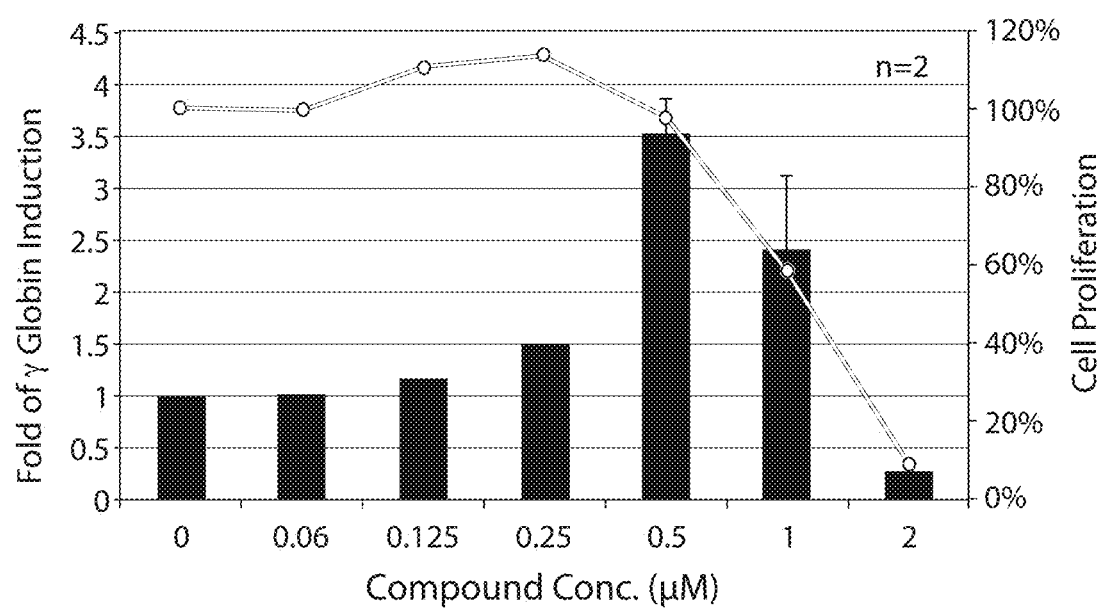
FIG. 9 is a graph showing dose-dependent γ-globin gene induction by exemplary compound AS-28, by the concentration of AS-28 compared with the fold level of γ-globin induction and percentage of cell proliferation in primary human erythroid cell cultures.

Compound AS-28 was designed based on the pharmacophore of the HbF-inducing compound TN1 (FIGS. 1A-1B). The efficacy of γ-globin gene induction by AS-28 treatment using a primary human erythroid cell culture system was evaluated. After two weeks of in vitro erythroid cell differentiation, cells were treated with AS-28 for three days and then harvested for quantitative RT-PCR analysis and cell viability assay. Fold-change of γ-globin mRNA expression in primary human erythroid cell cultures was significantly increased by AS-28 treatment in a dose-dependent manner, with working concentrations ranging from 0.06 µM to 0.5 µM (FIGS. 2 and 9, black bars). Higher concentrations, 1 µM and 2 µM, of AS-28 treatment resulted in cell cytotoxicity, which reduced γ-globin induction. Importantly, primary human erythroid cells treated with 0.5 µM AS-28 activated γ-globin mRNA expression 3.5-fold without inducing significant cytotoxicity.

Figure 3:
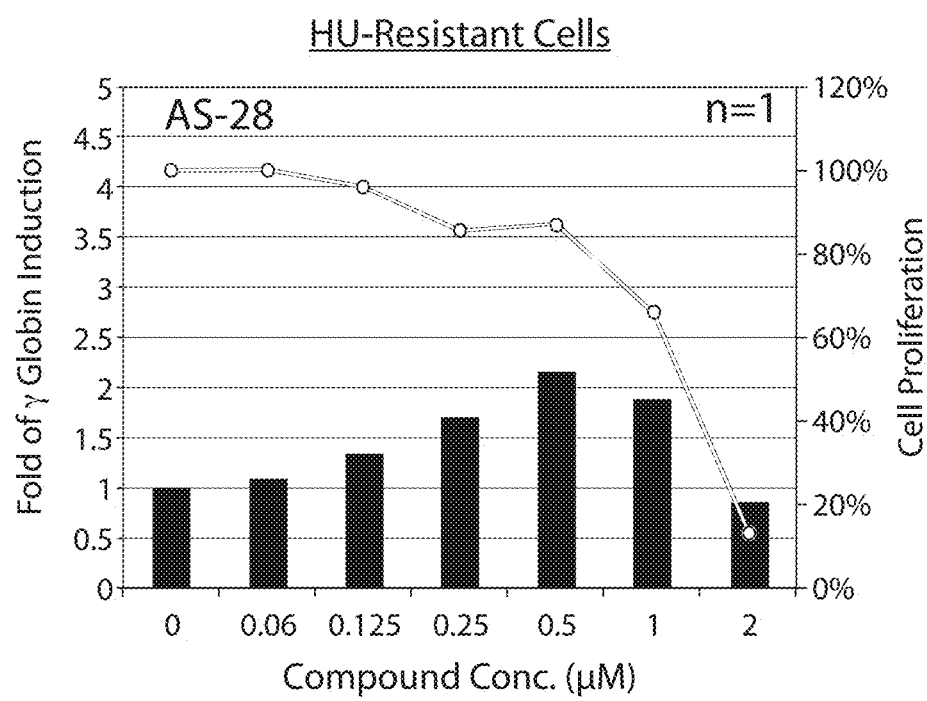
FIG. 3 is a graph showing that exemplary compound AS-28 (0.5 μM) induces γ-globin gene expression in hydroxyurea (HU)-resistant primary erythroid cells, by the concentration of AS-28 compared with the fold level of γ-globin induction and percentage of cell proliferation in primary human erythroid cell cultures (e.g., in HU-resistant primary human erythroid cells).
Figure 10:
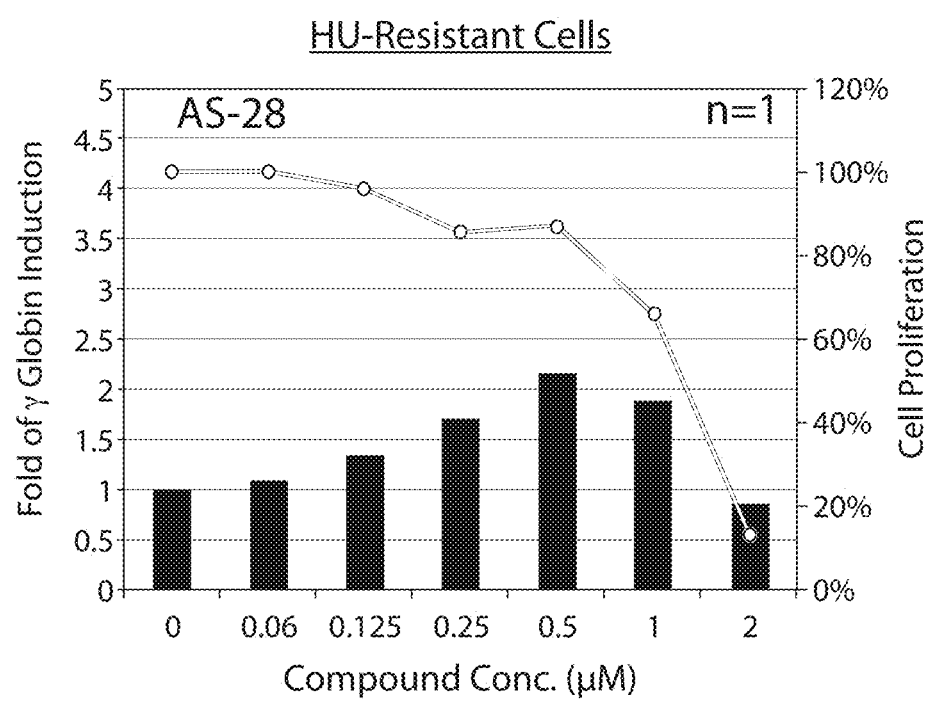
FIG. 10 is a graph showing that exemplary compound AS-28 (0.5 μM) induces γ-globin gene expression in hydroxyurea (HU)-resistant primary erythroid cells, by the concentration of AS-28 compared with the fold level of γ-globin induction and percentage of cell proliferation in primary human erythroid cell cultures (e.g., in HU-resistant primary human erythroid cells).

AS-28 Activates γ-Globin Expression in Hydroxyurea-Resistant Primary Human Erythroid Cells Since there are currently limited therapeutic options for SCD patients that are poorly- or non-responsive to HU, next the HbF-inducing capability of AS-28 in primary human erythroid cells that are non-responsive to HU treatment were examined. As shown in FIG. 3 and FIG. 10, AS-28 treatment (0.5 µM) elevated γ-globin mRNA expression at least 2-fold in HU-resistant cells with only minor cytotoxicity. This outcome demonstrated the advantage of using AS-28 to develop a new generation of therapeutic drugs that can be used in a broad range of patients with hemoglobinopathies, whether they are HU-responsive or HU-resistant.

BCL11A Protein Levels are Down-Regulated by AS-28 Treatment

Figure 4:
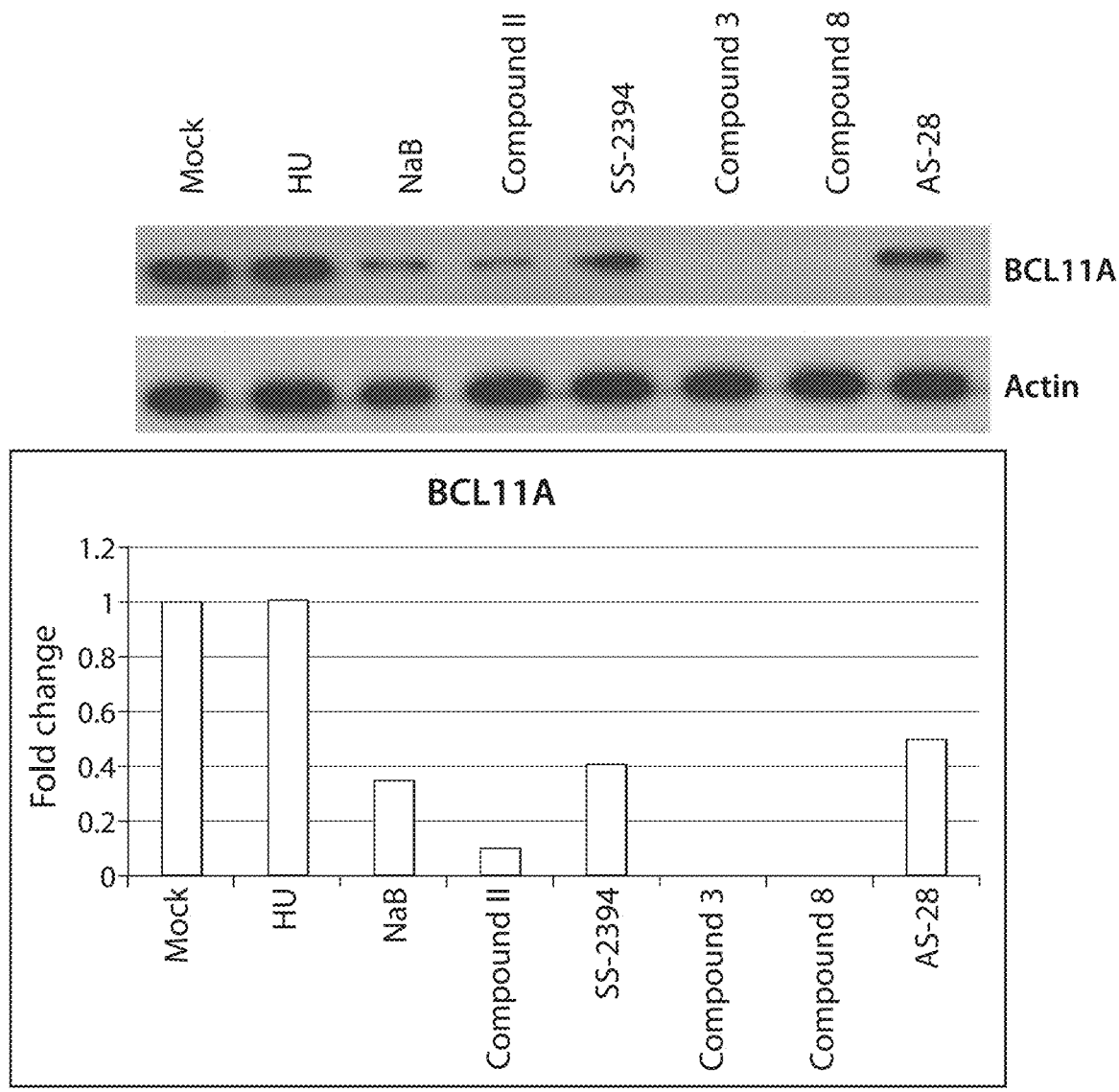
FIG. 4 is a blot of the expression levels of BCL11A protein compared with control actin, upon treating primary human erythroid cells with known HbF-inducing agents (HU, NaB, and AS-28), and treating with Compound II, SS-2394, Compound 3, and Compound 8.
Figure 11:
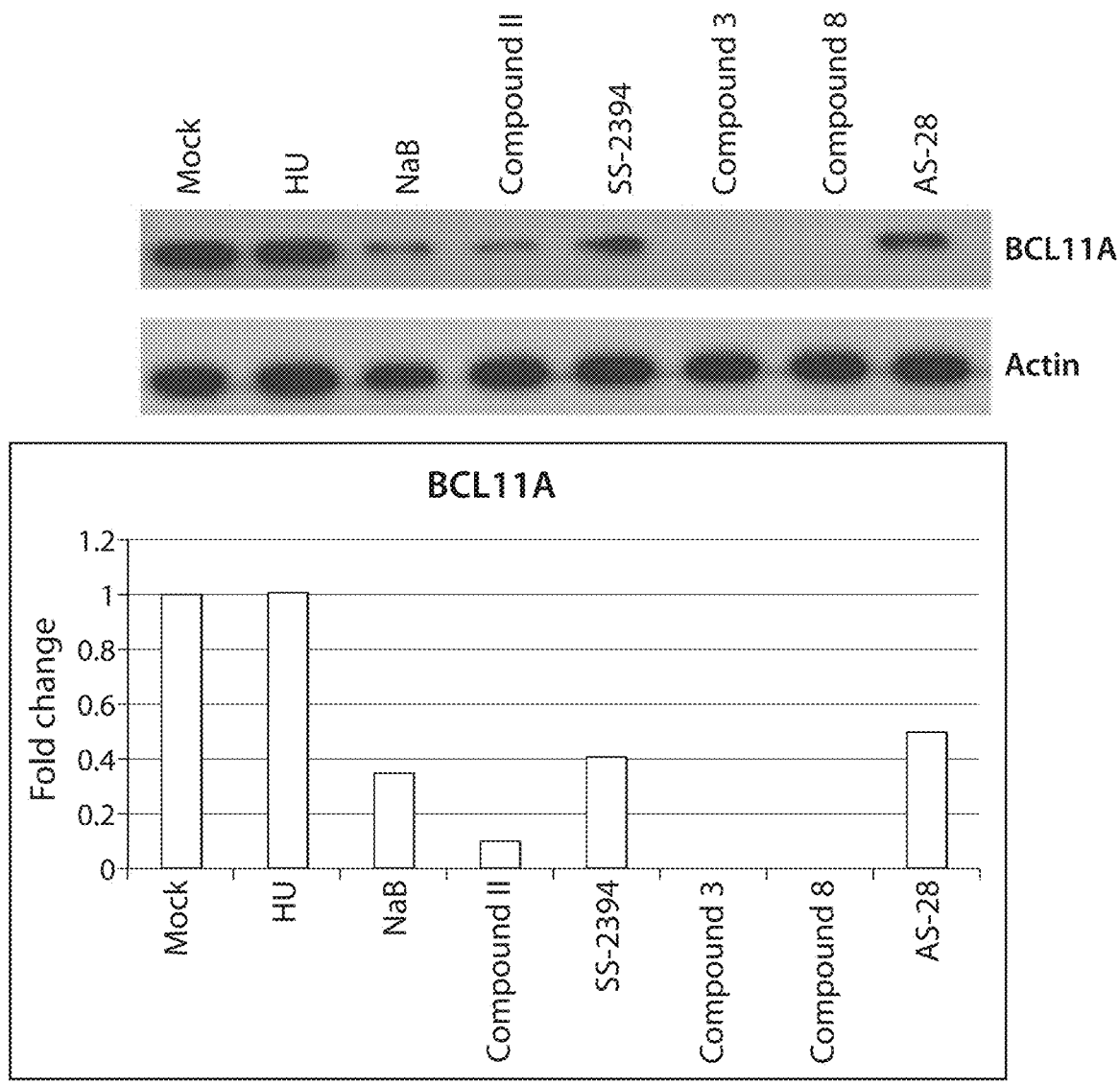
FIG. 11 is a blot of the expression levels of BCL11A protein compared with control actin, upon treating primary human erythroid cells with known HbF-inducing agents (HU, NaB) and treating with Compound II, SS-2394, Compound 3, Compound 8.

BCL11A has been reported as a key negative regulator of γ-globin gene expression[23]. Knockdown of BCL11A dramatically increases expression of the γ-globin gene. To investigate whether HbF-inducing agents activate γ-globin gene expression by modulating BCL11A protein levels, primary human erythroid cells were treated with known HbF-inducing agents (HU, NaB, and AS-28 (0.5 µM and 1 µM)), and also Compound II, SS-2394, Compound 3, Compound 8, and then harvested for Western blot analysis (FIG. 4; FIG. 11). The expression levels of BCL11A protein were significantly decreased upon treating cells with two of these HbF-inducing agents (HU, NaB, and AS-28), and also Compound II, SS-2394, Compound 3, Compound 8, with AS-28 treatment reducing BCL11A protein levels by 50% (FIG. 4) and reducing BCL11A protein levels by 60% (FIG. 11). This outcome suggests that AS-28 activates γ-globin gene expression, at least in part, by down-regulating the expression of the γ-globin negative regulator, BCL11A. There was no detectable change in BCL11A level in HU-treated erythroid cells, indicating that HU may activate γ-globin gene expression through another mechanism.

Oral Administration of AS-28 Significantly Relieves Symptoms of Anemia in SCD Mice.

To further evaluate the therapeutic potential of AS-28 for treating hemoglobinopathies, SCD mice (an SCD disease animal model generated by the laboratory of Prof. Tim Townes, University of Alabama) were used to examine whether AS-28 treatment could relieve anemia in SCD mice. Different dosages of AS-28 were administered to 6-8 week-old SCD mice over four weeks. After four weeks of oral gavage, blood samples from the treated SCD mice were collected for several biochemical analyses (FIG. 5). Complete blood cell assessment showed that AS-28 treatment slightly increased red blood cell (RBC) numbers and hemoglobin levels (HGB) in peripheral blood samples of SCD mice compared to those of mock-treated control mice. Reticulocyte (RET), white blood cell (WBC) and neutrophil (NEUT) values were equivalent between AS-28-treated and mock-treated SCD mice. HPLC analysis revealed that AS-28 significantly increased the percentage of HbF in SCD mice, which was consistent with the finding of an elevated percentage of F-cells in these mice, as detected by flow cytometry. A diagnostic indicator of SCD is the characteristic sickle-shaped morphology of red blood cells under hypoxia. A previous study demonstrated that over-expression of γ-globin can reduce the percentage of sickle-shaped red blood cells in the peripheral blood of SCD patients[24]. The percentages of sickle-shaped cells in SCD mouse blood smears under hypoxia were assessed, and it was found that this parameter was significantly decreased upon AS-28 treatment, indicating that AS-28 treatment might decrease the risk of vaso-occlusive crisis in SCD mice. Taken together, the in vivo experiments in SCD mice suggest that AS-28 has the potential to be developed into a new drug for treating SCD and β-thalassemia.

Analysis of AS-28 and Cellular Toxicity

Figure 7:
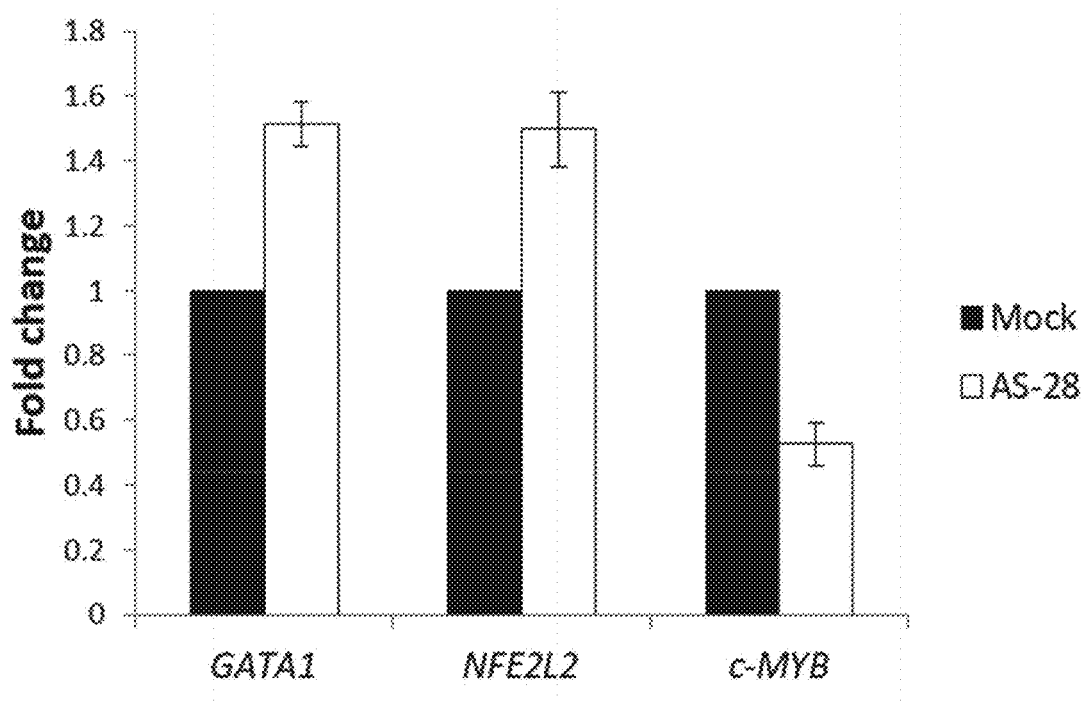
FIG. 7 shows RT-qPCR analysis of transcription regulators of γ-globin gene in human primary erythroid cells treated with AS-28 (0.5 μM). The total RNAs were isolated from human primary erythroid cells in culture without (Mock) and with (AS-28) treatment by AS-28, and analyzed by RT-qPCR. N=4 biological experiments, *, p<0.05; ***, p<0.001.

In order to examine whether AS-28 would cause cellular toxicity, the gene expression profiles of human primary erythroid cells in culture were compared by RNA-sequence analysis. Several candidate genes, encoding known γ globin gene regulators were selected from the gene list of RNA-sequence data (fold change >1.4) for validation by RT-qPCR (FIG. 7). The results showed that AS-28 induces γ globin activators GATA1 (1.5-fold) and NFE2L2 (1.5-fold). In addition, AS-28 inhibited the expression of γ globin repressor c-MYB (0.5-fold). The data of FIG. 7 indicates that AS-28 activates γ globin gene expression in part through modulating the expression of these three transcription regulators of γ globin gene.

To reveal the global effect of AS-28 on human primary erythroid cells, the differentially expressed genes (DEGs) from the RNA-sequence data (fold change ≥1.4 and p<0.05) were selected for analysis by Ingenuity Pathways Analysis (IPA). As seen in FIG. 8, the top 5 canonical pathways affected by AS-28 treatment of the primary human erythroid cells does not include the cell toxicity-related pathways, e.g. cell cycle arrest, DNA repair, DNA damage, etc.

Derivatives of AS-28

The invention described herein is based on the unexpected discovery that certain 2-amino-6-anilino-purine compounds efficiently induce γ-globin expression. FIG. 6 lists the exemplary representative compounds derived from this invention, each of which has been assigned a unique compound number.

Several pharmacophores were combined to design an exemplary new compound, AS-28. AS-28 exhibited improved water solubility and bioavailability. The in vitro assay demonstrated that AS-28 can efficiently induce γ-globin expression at a non-toxic concentration in primary erythroid cells. It was also found that AS-28 can induce γ-globin expression in HU-resistant cells. These findings support that AS-28 could represent a good candidate for development into new therapeutic compounds. The molecular mechanism by which AS-28 induces γ-globin expression was identified. According to a Western blot analysis, AS-28 reduces expression levels of BCL11A, which is a key repressor of γ-globin. To test the γ-globin-inducing efficacy of AS-28 in vivo, SCD mice were used as an animal model and AS-28 was designed as an orally-administered compound for drug development purposes. AS-28 was administered by oral gavage to SCD mice for 4 weeks. The results show that AS-28 improved several blood parameters in SCD mice. Thus, AS-28 is an exemplary compound as a candidate for treating SCD and β-thalassemia.

REFERENCES

1. Weatherall D J. Phenotype[mdash]genotype relationships in monogenic disease: lessons from the thalassaemias. *Nat Rev Genet.* 2001; 2(4):245-255.
2. Modell B. Global epidemiology of haemoglobin disorders and derived service indicators. *Bulletin of the World Health Organization.* 2008; 2008(6):480-487.
3. Patrinos G P, Grosveld F G. Pharmacogenomics and therapeutics of hemoglobinopathies. *Hemoglobin.* 2008; 32(1-2):229-236.
4. Schechter A N. Hemoglobin research and the origins of molecular medicine. *Blood.* 2008; 112(10):3927-3938.
5. Platt O S, Brambilla D J, Rosse W F, et al. Mortality in sickle cell disease. Life expectancy and risk factors for early death. *N Engl J Med.* 1994; 330(23):1639-1644.
6. Scott M D, van den Berg J J, Repka T, et al. Effect of excess alpha-hemoglobin chains on cellular and membrane oxidation in model beta-thalassemic erythrocytes. *J Clin Invest.* 1993; 91(4):1706-1712.
7. Aljurf M, Ma L, Angelucci E, et al. Abnormal assembly of membrane proteins in erythroid progenitors of patients with beta-thalassemia major. *Blood.* 1996; 87(5):2049-2056.
8. Natta C L, Niazi G A, Ford S, Bank A. Balanced globin chain synthesis in hereditary persistence of fetal hemoglobin. *J Clin Invest.* 1974; 54(2):433-438.
9. Noguchi C T, Rodgers G P, Serjeant G, Schechter A N. Levels of fetal hemoglobin necessary for treatment of sickle cell disease. *N Engl J Med.* 1988; 318(2):96-99.
10. Ley T J, Nienhuis A W. Induction of hemoglobin F synthesis in patients with beta thalassemia. *Annu Rev Med.* 1985; 36:485-498.
11. Humphries R K, Dover G, Young N S, et al. 5-Azacytidine acts directly on both erythroid precursors and progenitors to increase production of fetal hemoglobin. *J Clin Invest.* 1985; 75(2):547-557.
12. Olivieri N F, Weatherall D J. The therapeutic reactivation of fetal haemoglobin. *Hum Mol Genet.* 1998; 7(10):1655-1658.
13. McCaffrey P G, Newsome D A, Fibach E, Yoshida M, Su M S. Induction of gamma-globin by histone deacetylase inhibitors. *Blood.* 1997; 90(5):2075-2083.
14. Witt O, Monkemeyer S, Ronndahl G, et al. Induction of fetal hemoglobin expression by the histone deacetylase inhibitor apicidin. *Blood.* 2003; 101(5):2001-2007.
15. Constantoulakis P, Knitter G, Stamatoyannopoulos G. On the induction of fetal hemoglobin by butyrates: in vivo and in vitro studies with sodium butyrate and comparison of combination treatments with 5-AzaC and AraC. *Blood.* 1989; 74(6):1963-1971.
16. Grigg A. Effect of hydroxyurea on sperm count, motility and morphology in adult men with sickle cell or myeloproliferative disease. *Intern Med J.* 2007; 37(3):190-192.
17. Kinney T R, Helms R W, O'Branski E E, et al. Safety of hydroxyurea in children with sickle cell anemia: results of the HUG-KIDS study, a phase I/II trial. Pediatric Hydroxyurea Group. *Blood.* 1999; 94(5):1550-1554.
18. Steinberg M H, Lu Z H, Barton F B, Terrin M L, Charache S, Dover G J. Fetal hemoglobin in sickle cell anemia: determinants of response to hydroxyurea. Multicenter Study of Hydroxyurea. *Blood.* 1997; 89(3):1078-1088.
19. Rule H G, Thompson S B. Acenaphthenone and acenaphthenequtnone. *Journal of the Chemical Society.* 1937:1761-1763.
20. Bistrzycki A, Risi J. On the effect of various diamines on naphthalic acid anhydride. *Helvetica Chimica Acta.* 1925; 8:810-820.

21. Nam T-g, Lee J, Walker J R, Brinker A, Cho C Y, Schultz P G. Identification and Characterization of Small-Molecule Inducers of Fetal Hemoglobin. *ChemMedChem.* 2011; 6(5):777-780.
22. Fibach E, Prus E. Differentiation of Human Erythroid Cells in Culture. *Current Protocols in Immunology.* 2005; 69(1):22F.27.21-22F.27.10.
23. Basak A, Sankaran V G. Regulation of the fetal hemoglobin silencing factor BCL11A. *Annals of the New York Academy of Sciences.* 2016; 1368(1):25-30.
24. Akinsheye I, Alsultan A, Solovieff N, et al. Fetal hemoglobin in sickle cell anemia. *Blood.* 2011; 118:19-27.
25. Imbach P, Capraro H G, Zimmermann J, Caravatti G, Furet P, Brill W, (Novartis-Erfindungen; Vienna, Austria), PCT document: WO/2000/049018A1, 2000; Published patents: EP1153024B1, 2004; U.S. Pat. No. 6,767,906B2, 2004.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control.

In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:
1. A compound of Formula (I):

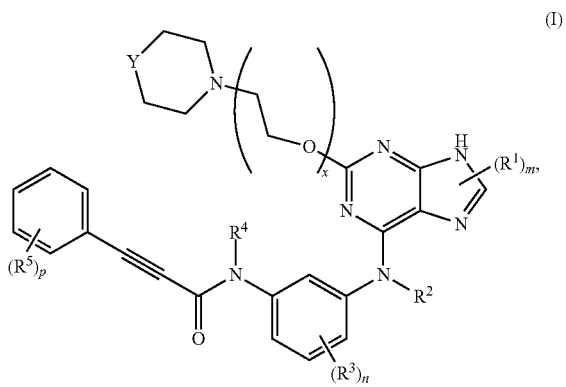

or a pharmaceutically acceptable salt thereof, wherein:
each instance of $R^1$ is independently halogen, —C(=O) (alkyl); alkyl optionally substituted with halogen, unsubstituted alkenyl, unsubstituted alkynyl, or a nitrogen protecting group when attached to a nitrogen atom;
$R^2$ is hydrogen, unsubstituted alkyl, or a nitrogen protecting group;
each instance of $R^3$ is independently halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$OR^{D1}$, —$N(R^{D1a})_2$, or —$SR^{D1}$;
$R^4$ is hydrogen, unsubstituted alkyl, or a nitrogen protecting group;
each instance of $R^5$ is independently halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$OR^{D1}$, —$N(R^{D1a})_2$, or —$SR^{D1}$,
$R^{D1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each occurrence of $R^{D1a}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two instances of $R^{D1a}$ are taken together with their intervening atoms to form a substituted or unsubstituted heterocyclic or substituted or unsubstituted heteroaryl ring;

Y is —O— or —N($R^6$)—;

$R^6$ is hydrogen, optionally substituted alkyl, or a nitrogen protecting group;

p is 0, 1, 2, 3, 4, or 5;

m is 0, 1, or 2;

n is 0, 1, 2, 3, or 4; and x is 0, 1, or 2.

2. The compound of claim 1, wherein at least one instance of $R^1$ is unsubstituted $C_{1-6}$ alkyl.

3. The compound of claim 1, wherein at least one instance of $R^1$ is unsubstituted ethyl.

4. The compound of claim 1, wherein m is 1.

5. The compound of claim 1, wherein $R^2$ is hydrogen.

6. The compound of claim 1, wherein n is 0.

7. The compound of claim 1, wherein $R^4$ is hydrogen.

8. The compound of claim 1, wherein at least one instance of $R^5$ is unsubstituted $C_{1-6}$ alkyl.

9. The compound of claim 1, wherein at least one instance of $R^5$ is unsubstituted methyl.

10. The compound of claim 1, wherein p is 1.

11. The compound of claim 1, wherein x is 0.

12. The compound of claim 1, wherein x is 1.

13. The compound of claim 1, wherein Y is O.

14. The compound of claim 1, wherein Y is —N($R^6$)—, and $R^6$ is optionally substituted $C_{1-6}$ alkyl.

15. The compound of claim 14, wherein Y is —N($R^6$)—, and $R^6$ is unsubstituted $C_{1-6}$ alkyl.

16. The compound of claim 15, wherein Y is —N(unsubstituted ethyl)-.

17. The compound of claim 1, wherein Y is —N($R^6$)—, and R is $C_{1-6}$ alkyl optionally substituted with —OH or —O(unsubstituted $C_{1-6}$ alkyl).

18. The compound of claim 17, wherein Y is —N(CH₂CH₂OH)—.

19. The compound of claim 1, wherein the compound is of formula:

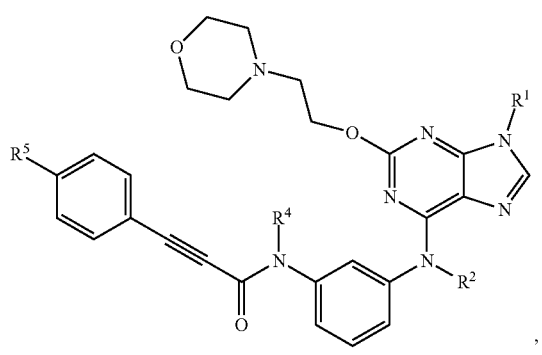

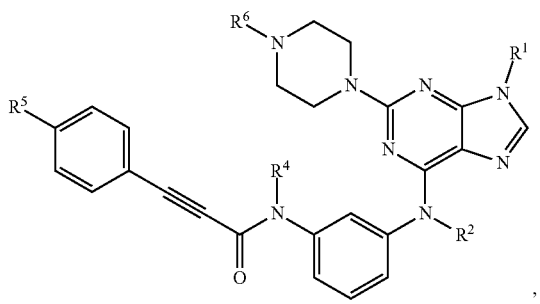

or a pharmaceutically acceptable salt thereof.

20. The compound of claim 1, wherein the compound is of formula:

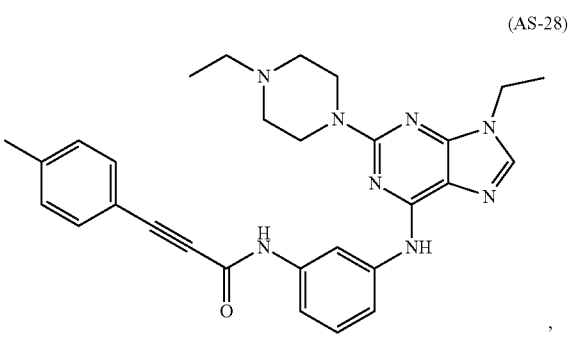

(AS-28)

(AS-61)

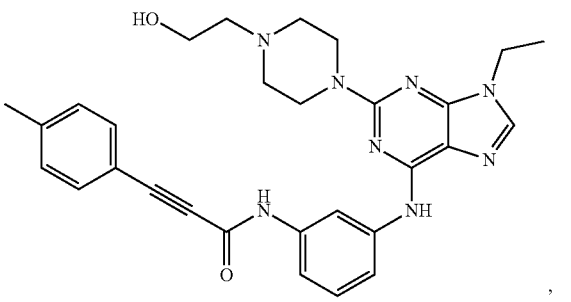

(AS-29)

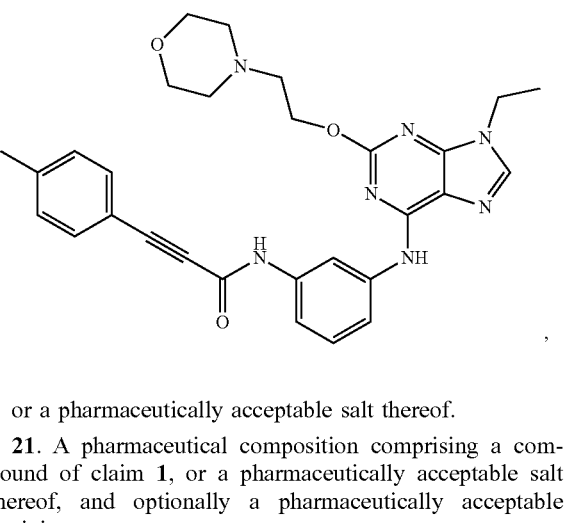

or a pharmaceutically acceptable salt thereof.

21. A pharmaceutical composition comprising a compound of claim 1, or a pharmaceutically acceptable salt thereof, and optionally a pharmaceutically acceptable excipient.

22. The pharmaceutical composition of claim 21, wherein the pharmaceutical composition comprises a therapeutically effective amount of the compound for treating a disease in a subject in need thereof.

23. The pharmaceutical composition of claim 22, wherein the disease is anemia.

24. A method of treating anemia in a subject in need thereof, the method comprising administering to the subject a therapeutically effective amount of a compound of claim 1, or a pharmaceutically acceptable salt prodrug thereof.

25. The method of claim 24, wherein the subject suffers from or is suspected of having β-thalassemia.

26. The method of claim 24, wherein the subject suffers from or is suspected of having sickle cell anemia.

27. The method of claim 24, wherein the pharmaceutical composition is administered orally.

28. The method of claim 24, wherein the pharmaceutical composition is administered parentally.

29. The method of claim 24, wherein the pharmaceutical composition is administered in combination with an additional therapeutic agent.

30. A kit comprising:
a compound of claim 1, or a pharmaceutically acceptable salt thereof; and
instructions for administering to a subject or contacting a biological sample with the compound, or the pharmaceutically acceptable salt, solvate, hydrate, tautomer, or stereoisomer thereof.

31. A method of treating anemia in a subject in need thereof, the method comprising administering to the subject a pharmaceutical composition of claim 21.

32. A kit comprising:
a pharmaceutical composition of claim 21; and
instructions for administering the pharmaceutical composition to a subject or contacting a biological sample with the pharmaceutical composition.

* * * * *